(12) United States Patent
Byun et al.

(10) Patent No.: US 10,702,546 B2
(45) Date of Patent: Jul. 7, 2020

(54) BILE ACID OLIGOMER CONJUGATE FOR NOVEL VESICULAR TRANSPORT AND USE THEREOF

(71) Applicant: ST PHARM CO., LTD., Siheung-si (KR)

(72) Inventors: Young Ro Byun, Seoul (KR); Al-Hilal Taslim Ahmed, Seoul (KR); Ok Cheol Jeon, Seoul (KR); Hyun Tae Moon, Seoul (KR); Kyungjin Kim, Siheung-si (KR); Jisuk Yun, Siheung-si (KR)

(73) Assignee: ST PHARM CO., LTD., Siheung-Si, Gyeonggi-do (KR)

( * ) Notice: Subject to any disclaimer, the term of this patent is extended or adjusted under 35 U.S.C. 154(b) by 0 days.

(21) Appl. No.: 14/437,477

(22) PCT Filed: Nov. 29, 2012

(86) PCT No.: PCT/KR2012/010265
§ 371 (c)(1),
(2) Date: Apr. 21, 2015

(87) PCT Pub. No.: WO2014/084421
PCT Pub. Date: Jun. 5, 2014

(65) Prior Publication Data
US 2015/0290335 A1 Oct. 15, 2015

(51) Int. Cl.
*A61K 31/727* (2006.01)
*C07K 14/62* (2006.01)
(Continued)

(52) U.S. Cl.
CPC .......... *A61K 31/727* (2013.01); *A61K 9/0053* (2013.01); *A61K 38/16* (2013.01);
(Continued)

(58) Field of Classification Search
CPC ...... A61K 31/727; A61K 38/16; A61K 38/26; A61K 47/48123; A61K 47/48038;
(Continued)

(56) References Cited

U.S. PATENT DOCUMENTS 6,653,457 B1 * 11/2003 Larm .................. A61L 33/08
525/54.2
6,656,922 B2 12/2003 Byun et al. .................. 514/12
(Continued)

FOREIGN PATENT DOCUMENTS

EP 793967 9/1997
KR 10-2009-0003128 1/2009

OTHER PUBLICATIONS

Janout et al., Bioconjugate-Based Molecular Umbrellas, Bioconjugate Chem., vol. 20(2):183-192 (online Nov. 20, 2008).*
(Continued)

*Primary Examiner* — Randall L Beane
(74) *Attorney, Agent, or Firm* — Dentons US LLP; Stephanie Seidman

(57) ABSTRACT

The present invention relates to a method for preparing an end site-specific macromolecule-bile acid oligomer conjugate, comprising conjugating a bile acid oligomer which is prepared by oligomerization of two or more bile acid monomers to the terminal site of a macromolecule; a method for body absorption of an end site-specific macromolecule-bile acid oligomer conjugate, comprising administering the macromolecule-bile acid oligomer conjugate prepared by the above method to a subject orally; an end site-specific macromolecule-bile acid oligomer conjugate wherein the bile acid oligomer is conjugated to the terminal site of macromolecule; a composition comprising the conjugate; an oral formulation for macromolecule comprising the conjugate, a solubilizer, an excipient, a disintegrant, a binder, and a lubricant; a pharmaceutical composition comprising a
(Continued)

heparin-bile acid oligomer conjugate wherein the bile acid oligomer is conjugated to the terminal site of heparin; and a method for treating thrombosis using said composition.

10 Claims, 16 Drawing Sheets

(51) Int. Cl.
　　C07K 14/605　　(2006.01)
　　A61K 9/00　　(2006.01)
　　A61K 49/04　　(2006.01)
　　B82Y 5/00　　(2011.01)
　　A61K 47/54　　(2017.01)
　　A61K 38/16　　(2006.01)
　　A61K 38/26　　(2006.01)

(52) U.S. Cl.
　　CPC ............ *A61K 38/26* (2013.01); *A61K 47/542* (2017.08); *A61K 47/554* (2017.08); *A61K 49/0423* (2013.01); *B82Y 5/00* (2013.01); *C07K 14/605* (2013.01); *C07K 14/62* (2013.01)

(58) Field of Classification Search
　　CPC .............. A61K 49/0423; A61K 9/0053; C07K 14/605; C07K 14/62; C08B 37/0075; B82Y 5/00
　　See application file for complete search history.

(56) References Cited

U.S. PATENT DOCUMENTS

| 8,088,753 | B2 | 1/2012 | Byun et al. .................... 514/169 |
| 2009/0149423 | A1 | 6/2009 | Byun et al. ...................... 514/56 |
| 2009/0149537 | A1 | 6/2009 | Gilat .............................. 514/558 |
| 2010/0021538 | A1* | 1/2010 | Byun ................... A61K 9/1641 424/463 |
| 2012/0232169 | A1 | 9/2012 | Wu et al. ....................... 424/482 |

OTHER PUBLICATIONS

Cline et al., A Molecular Umbrella Approach to the Intracellular Delivery of Small Interfering RNA, Bioconjugate Chemistry, vol. 22: 2210-2216 (Oct. 11, 2011).*
Linhardt, Chapter 20. Chemical and Enzymatic Methods for the Depolymerization and Modification of Heparin, Carbohydrates-Synthetic Methods and Applications in Medicinal Chemistry, published 1992, 18 pages.*
Maheshwari et al., Indian Journal of Pharmaceutical Sciences, Sep.-Oct. 2010, 649-651.*
Grotzky et al., Quantification of α-polylysine: a comparison of four UV/Vis spectrophotometric methods, Anal. Methods, vol. 2:1448-1455 (2010) (Year: 2010).*
Jenkins et al.; Glossary of Basic Terms in Polymer Science, IUPAC Macromolecular Division, Pure & Appl. Chem., vol. 68(12):2287-231 (1996) (Year: 1996).*
Moss et al., Glossary of Class Names of Organic Compounds and Reactive Intermediates Based on Structure, IUPAC Organic Chemistry Division, Pure & Appl. Chem., vol. 67(8/9):1307-1375 (1995) (Year: 1995).*
Sievanen, Exploitation of Bile Acid Transport Systems in Prodrug Design, Molecules, vol. 12:1859-1889 (2007) (Year: 2007).*
Kim et al., Physicochemical Conjugation with Deoxycholic Acid and Dimethylsulfoxide for Heparin Oral Delivery, Bioconjugate Chem., vol. 22:1451-1458 (May 31, 2011) (Year: 2011).*
Letter/Written Disclosure of the Supplemental Information Disclosure Statement for the above-referenced application, filed herewith on Sep. 1, 2016, 2 pages.
Kim et al., "Enhancing Effect of Chemically Conjugated Deoxycholic Acid on Permeability of Calcitonin in Caco-2 Cells." Drug Dev Res 64:129-135 (2005).
Lee et al., "Synthesis and Biological Properties of Insulin-Deoxycholic Acid Chemical Conjugates." Bioconjugate Chem. 16: 615-620 (2005).
Extended European Search Report, dated Mar. 31, 2016, in connection with European Patent Application No. 12889309.6, 8 pages.
Letter/Written Disclosure of the Information Disclosure Statement for the above-referenced application, dated Aug. 4, 2015, 2 pages.
Berkowitz et al., "Oral heparin administration with a novel drug delivery agent (SNAC) in healthy volunteers and patients undergoing elective total hip arthroplasty." J Thromb Haemost. 1(9):1914-1919 (2003).
Fini et al., "Basic cholane derivatives. XI: Comparison between acid and basic derivatives." J Pharm Sci. 81(7):726-730 (1992).
Kalia, J. and Raines, R. "Advances in Bioconjugation." Curr Org Chem. 14(2):138-147 (2010).
Kim et al., "Absorption study of deoxycholic acid-heparin conjugate as a new form of oral anti-coagulant," J Control Release. 120(1-2):4-10 (2007).
Linhardt, R., "Heparin-induced cancer cell death." Chem Biol. 11(4):420-422 (2004).
Park et al., "Strategies for oral delivery of macromolecule drugs," Biotechnology and Bioprocess Engineering 15(1):66-75 (2010).
Ross, B. and Toth, I. "Gastrointestinal absorption of heparin by lipidization or coadministration with penetration enhancers." Curr Drug Deliv. 2(3):277-287 (2005).
Velleste et al., "Reducing end-specific fluorescence labeled celluloses for cellulase mode of action," Cellulose 17:125-138 (2010).
Zhu, X. and Nichifor, M. "Polymeric materials containing bile acids," Acc Chem Res. 35(7):539-546 (2002).
International Search Report and Written Opinion, dated Aug. 20, 2013, in connection with International Application No. PCT/KR2012/010265, 12 pages.
International Preliminary Report on Patentability, dated Jun. 2, 2015, in connection with International Application No. PCT/KR2012/010265, 9 pages.
Letter/Written Disclosure of the Supplemental Information Disclosure Statement for the above-referenced application, filed herewith on Apr. 11, 2017, 2 pages.
Response, filed Oct. 26, 2016, to Communication Pursuant to Rules 70(2) and 70a(2) EPC, dated Apr. 19, 2016, in connection with corresponding European Patent Application No. 12889309.6, 16 pages.
Response, filed Apr. 6, 2017, to Communication Pursuant to Article 94(3) EPC (Examination Report), dated Dec. 13, 2016, in connection with corresponding European Patent Application No. 12889309. 6, 9 pages.
Letter/Written Disclosure of the Supplemental Information Disclosure Statement for the above-referenced application, filed herewith on Mar. 10, 2017, 3 pages.
Communication Pursuant to Article 94(3) EPC (Examination Report), dated Dec. 13, 2016, in connection with corresponding European Patent Application No. 12 889 309.6, 4 pages.
Letter/Written Disclosure of the Supplemental Information Disclosure Statement for the above-referenced application, filed herewith on May 22, 2018, 2 pages.
Intention to Grant (Communication under Rule 71(3) EPC), dated Apr. 23, 2018, in connection with corresponding European Patent Application No. 12 889 309.6, 61 pages.

* cited by examiner

[Fig. 1]
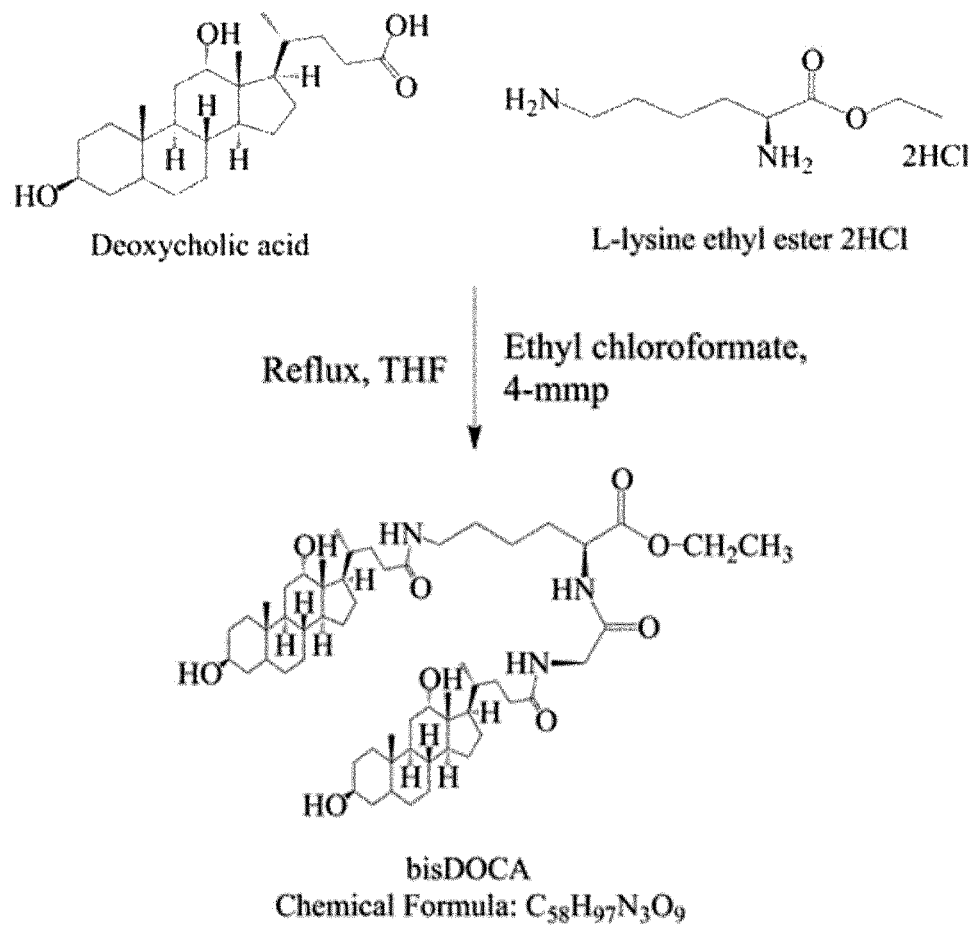
[Fig. 2]
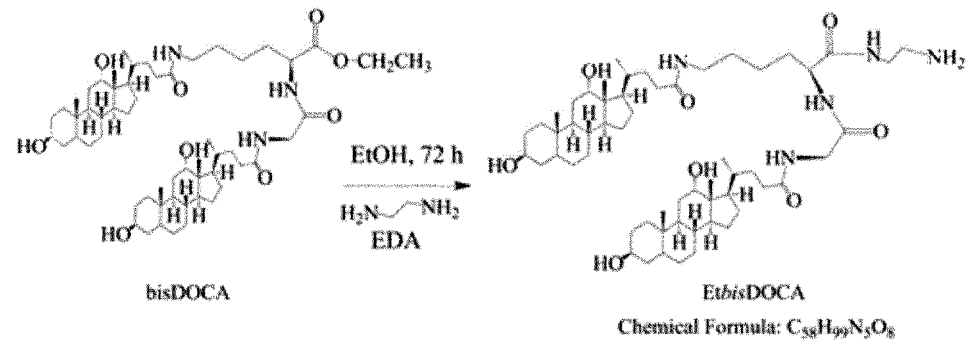

[Fig. 3]
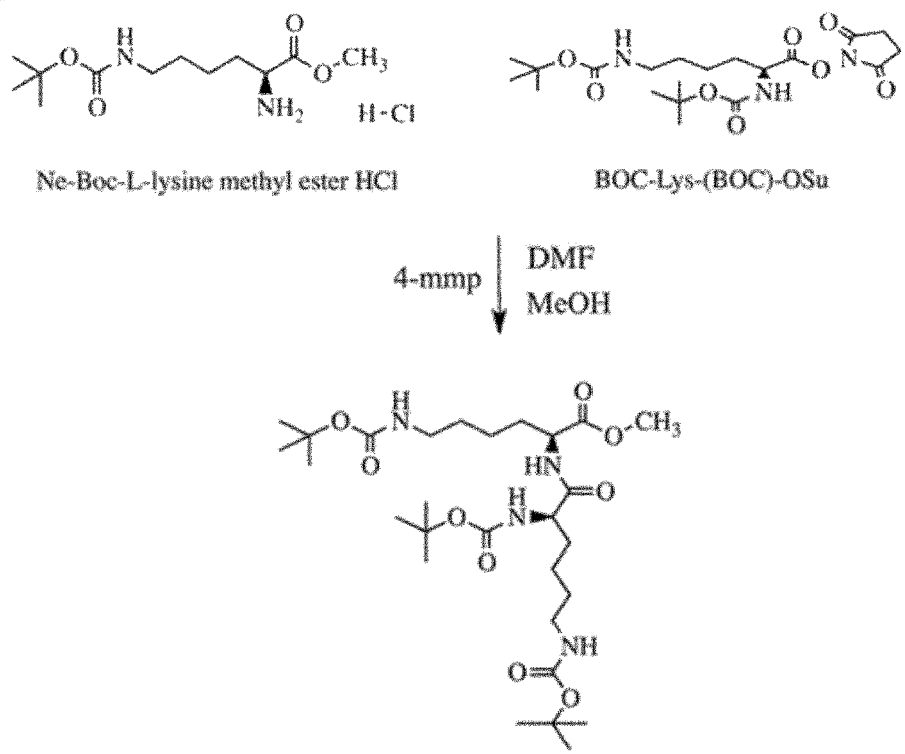
[Fig. 4]
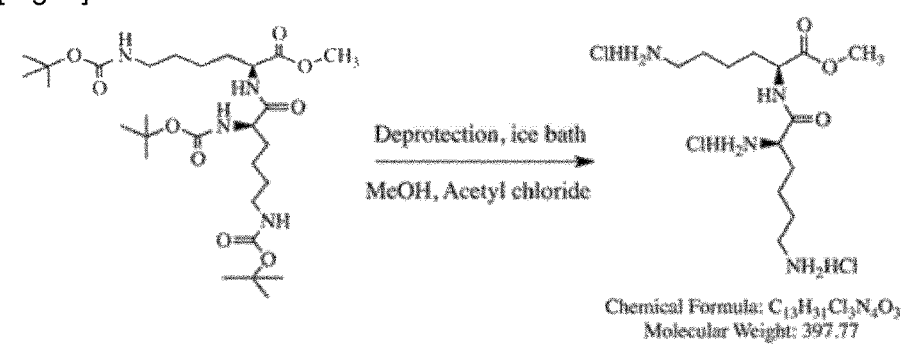
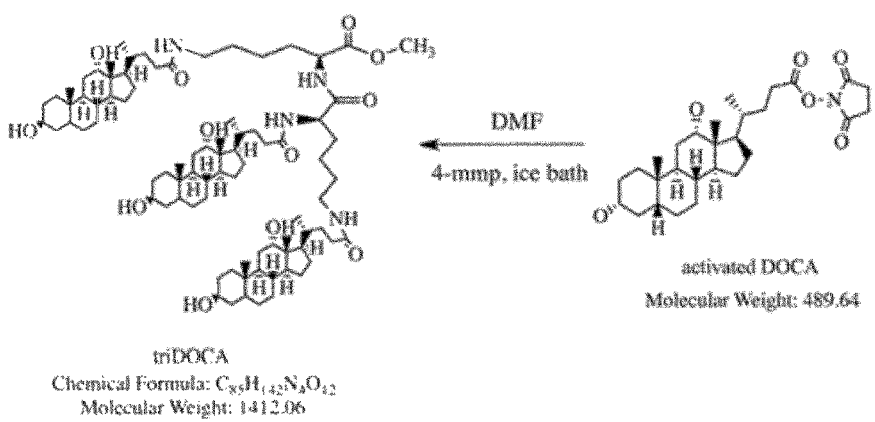

[Fig. 5]
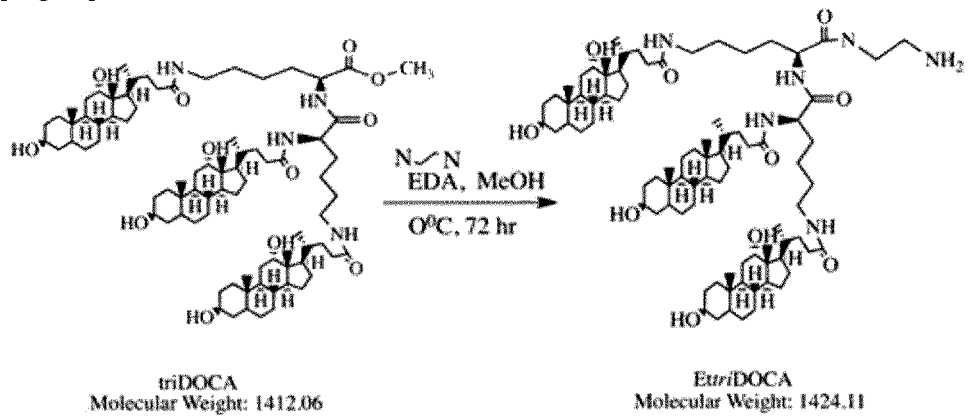
[Fig. 6]
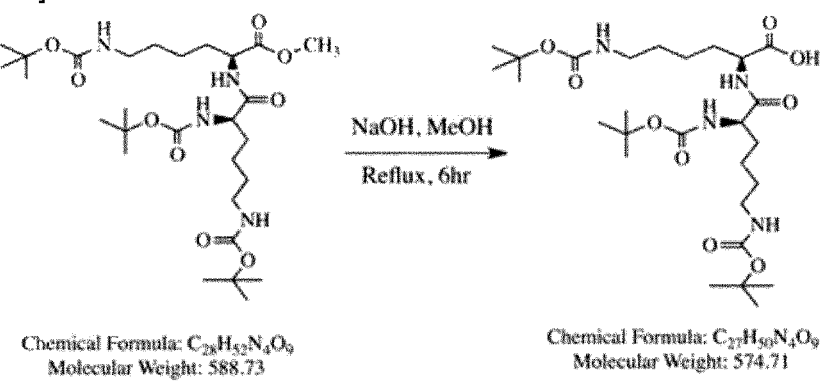
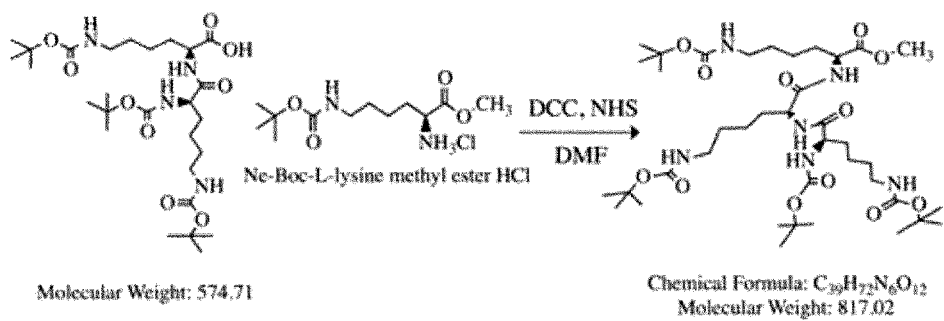

[Fig. 7]
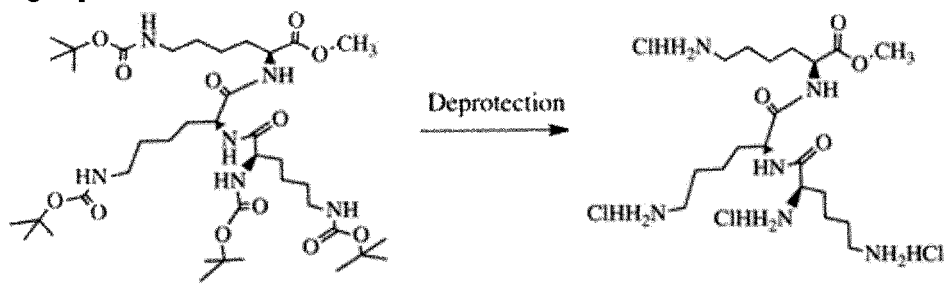
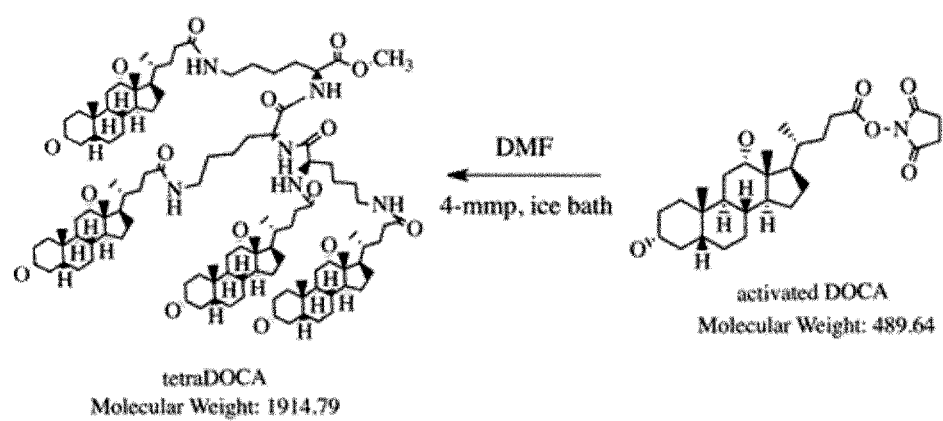
[Fig. 8]
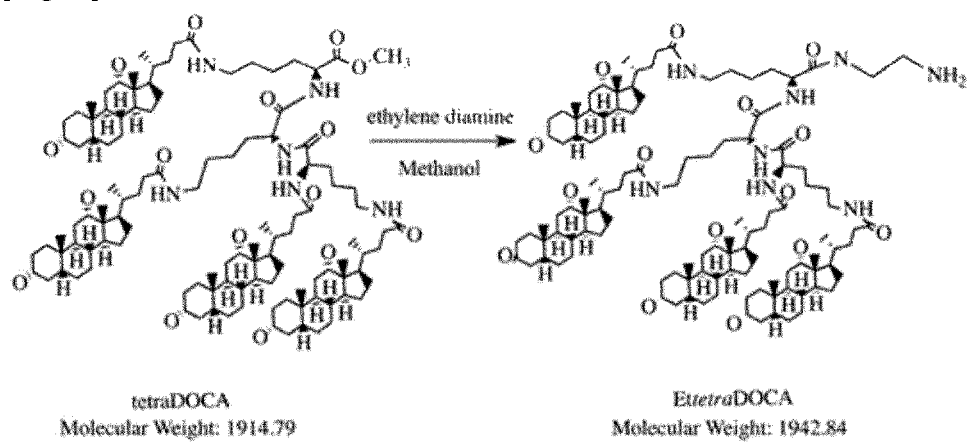

[Fig. 9]
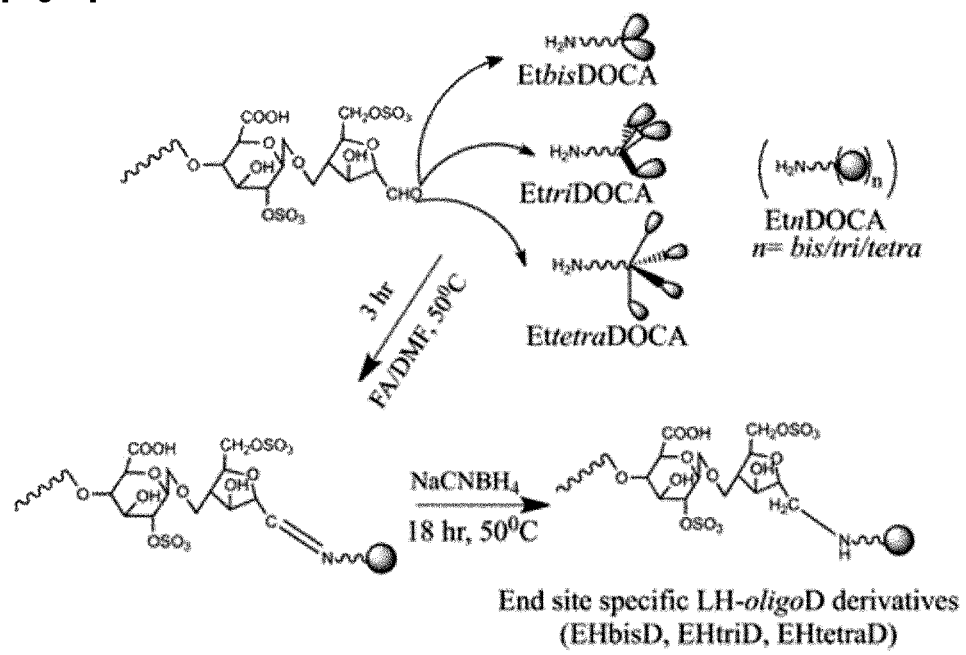
[Fig. 10]
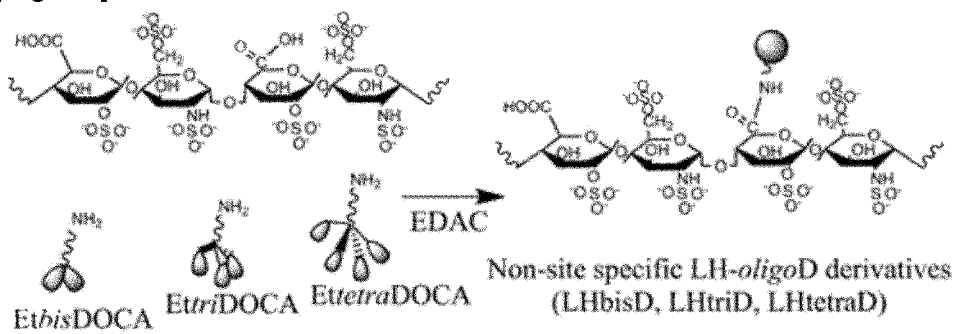

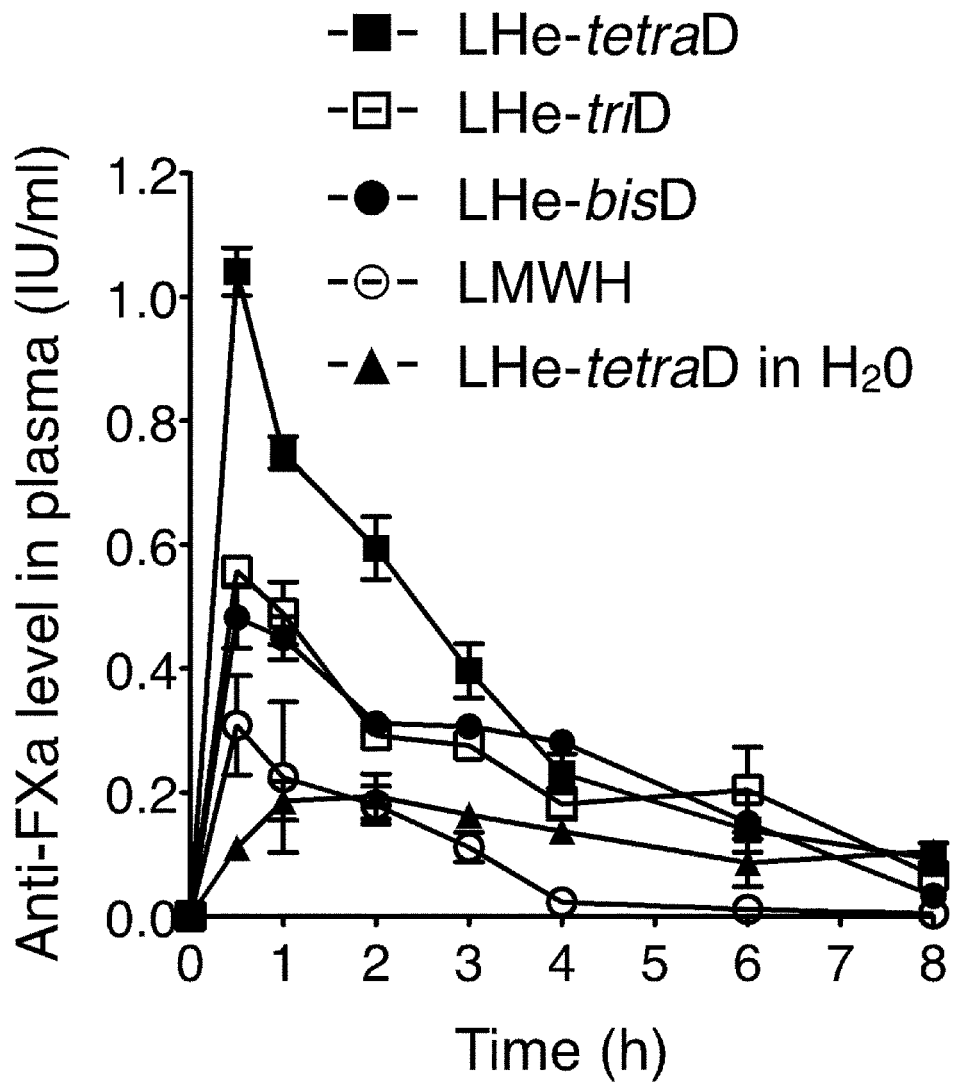
[Fig. 11]

[Fig. 12]
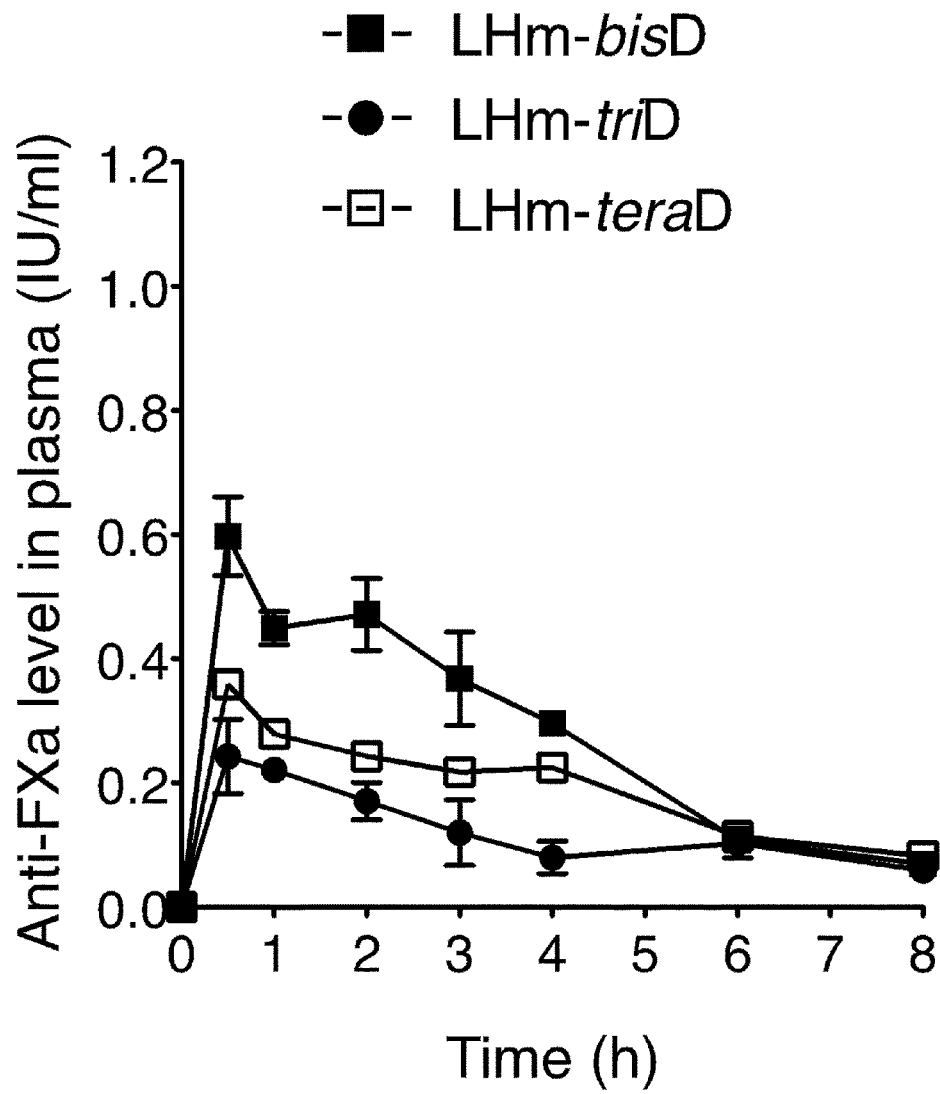

[Fig. 13]
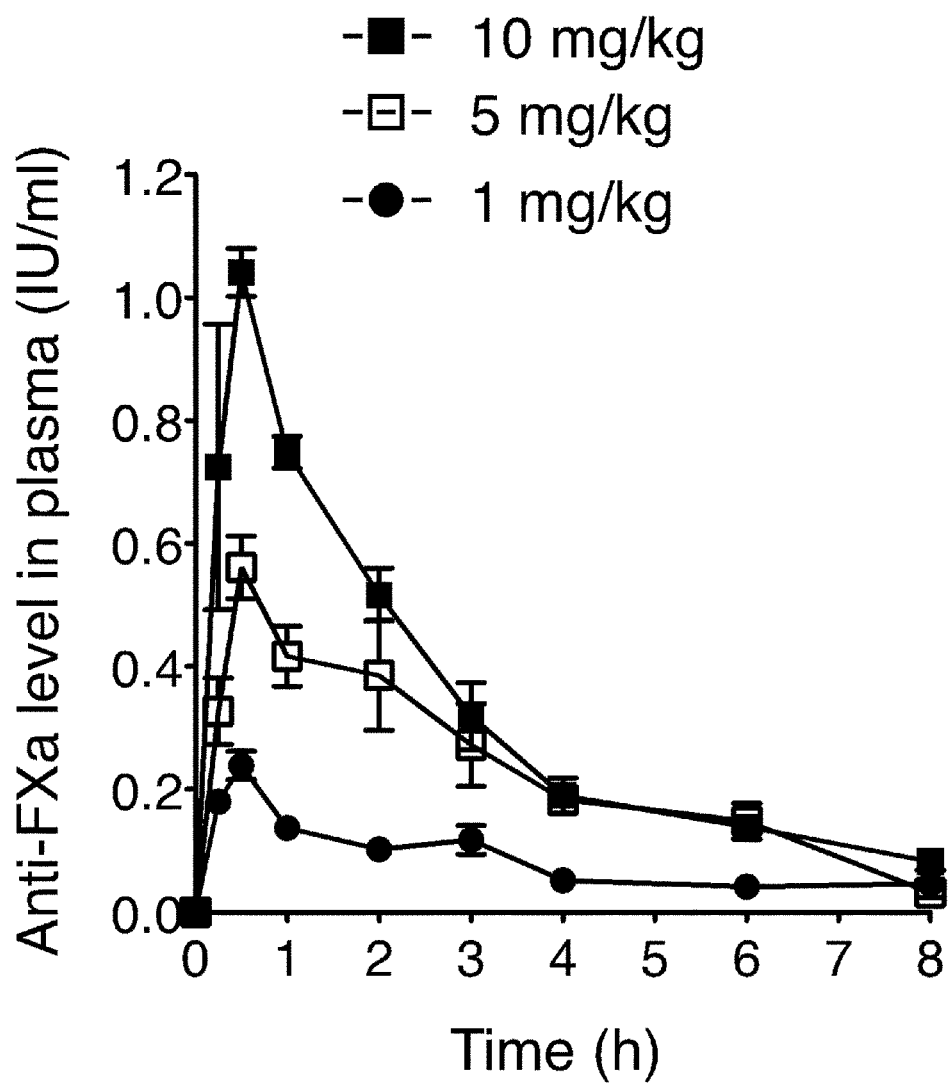

[Fig. 14]
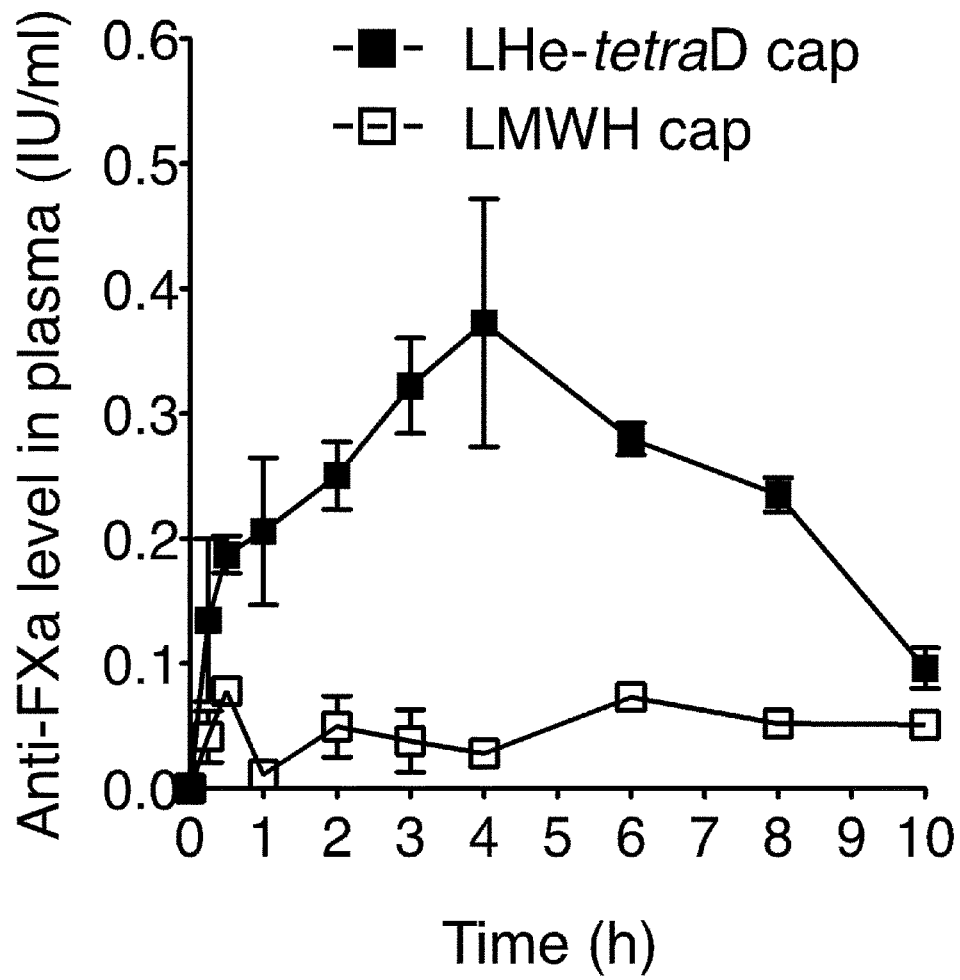
[Fig. 15]
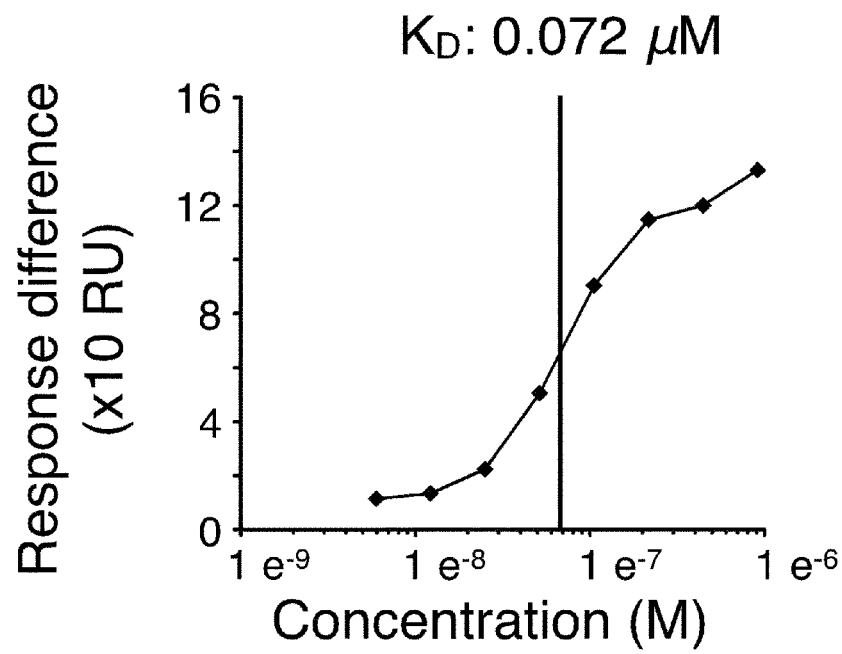

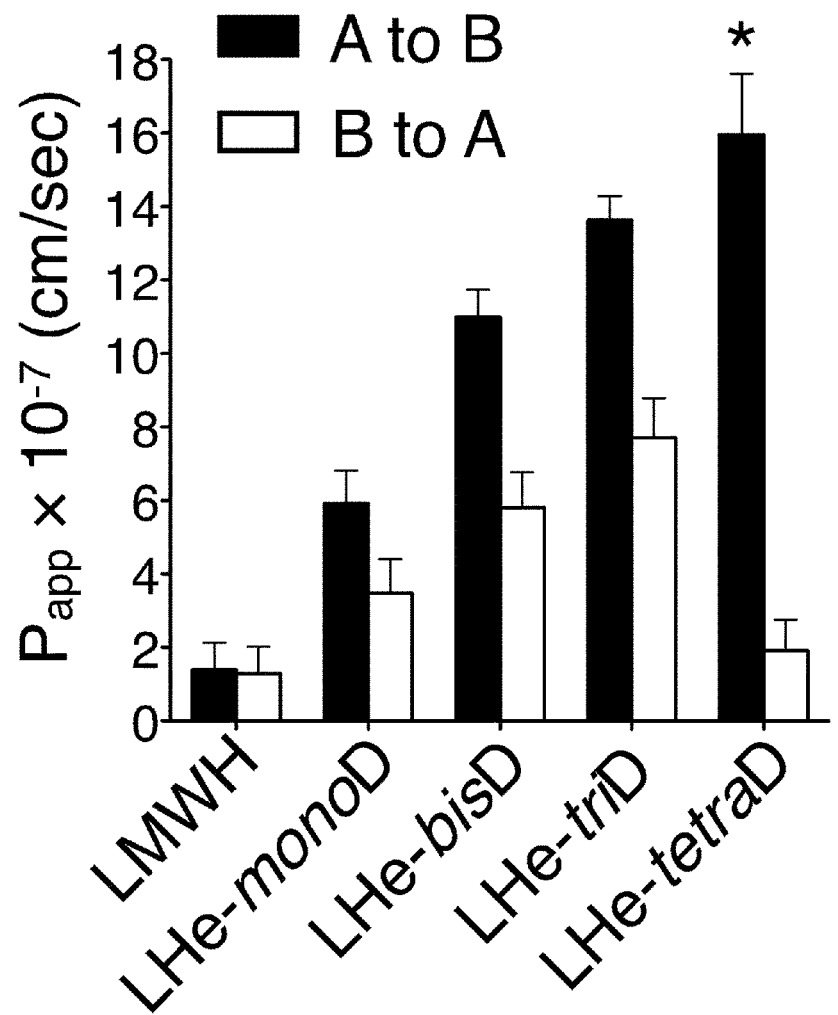
[Fig. 16]

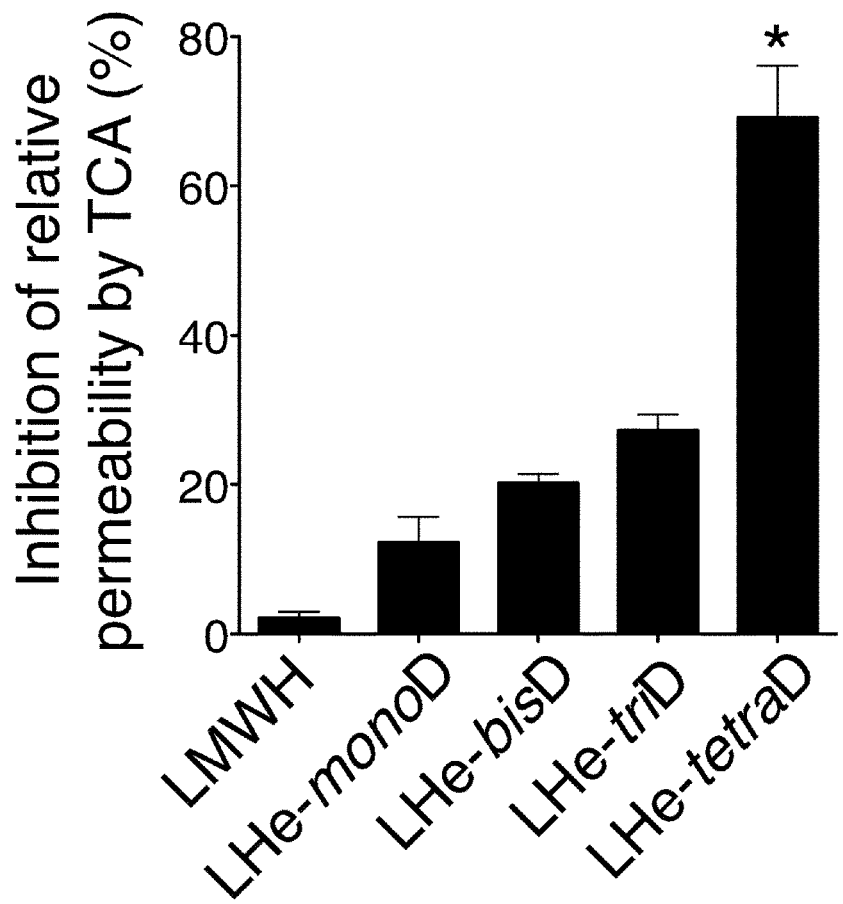
[Fig. 17]

[Fig. 18]
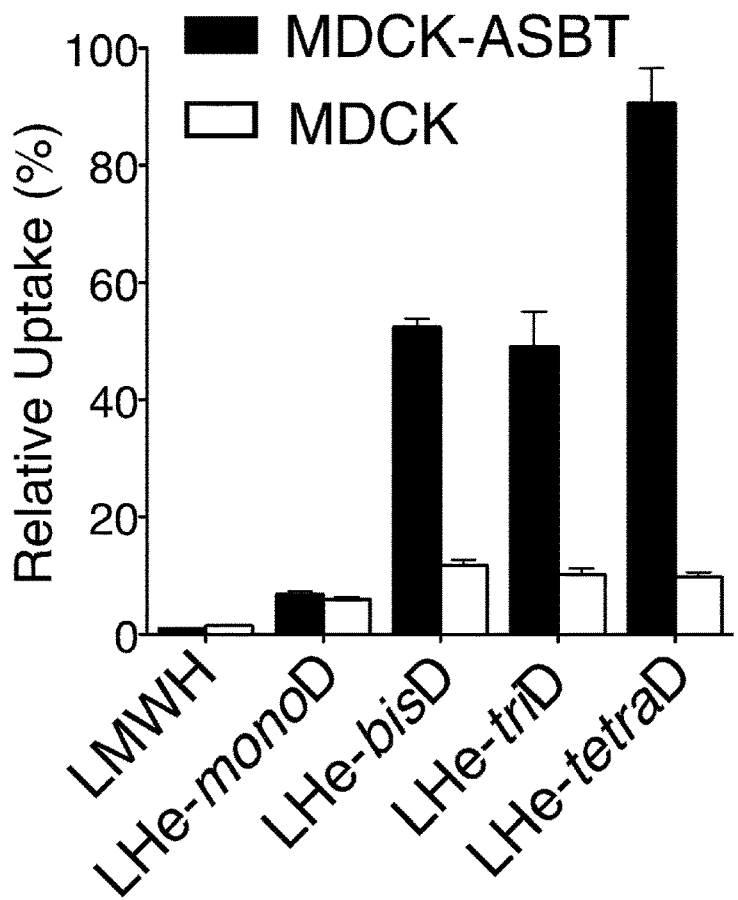
[Fig. 19]
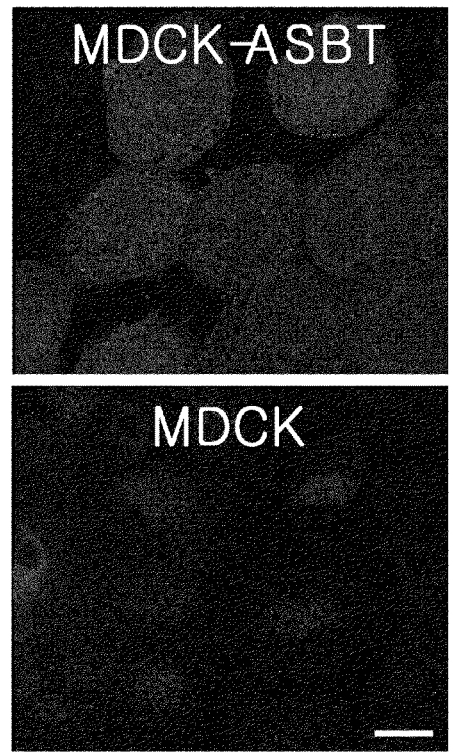

[Fig. 20]
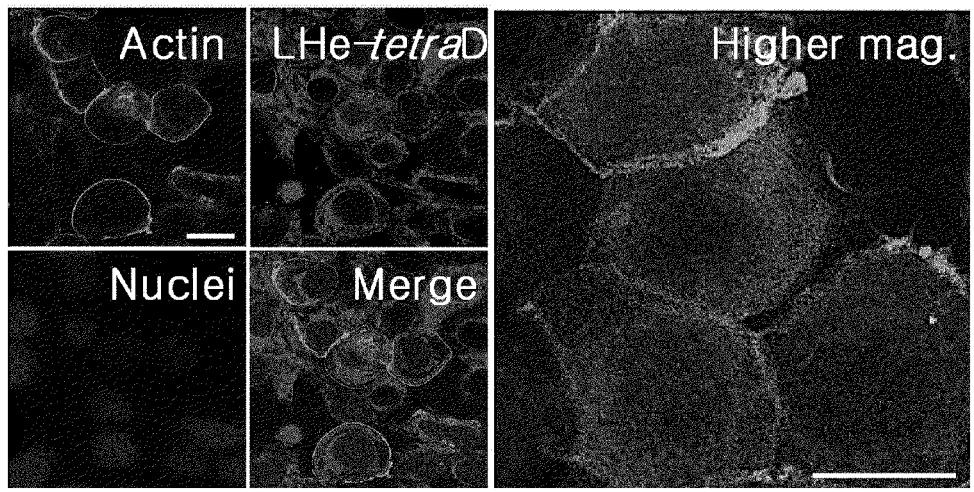
[Fig. 21]
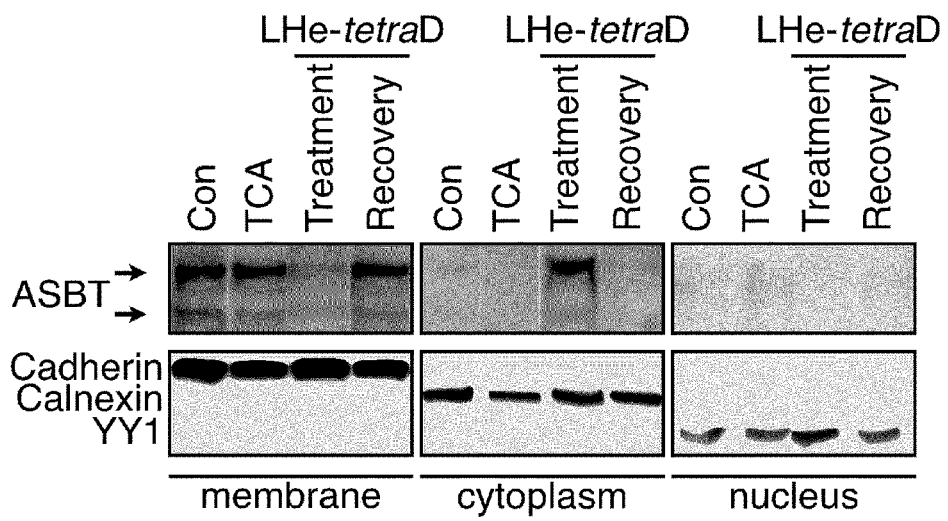
[Fig. 22]
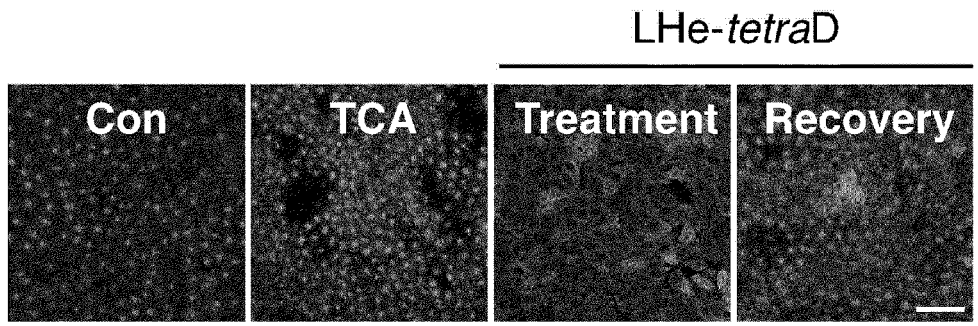

[Fig. 23]
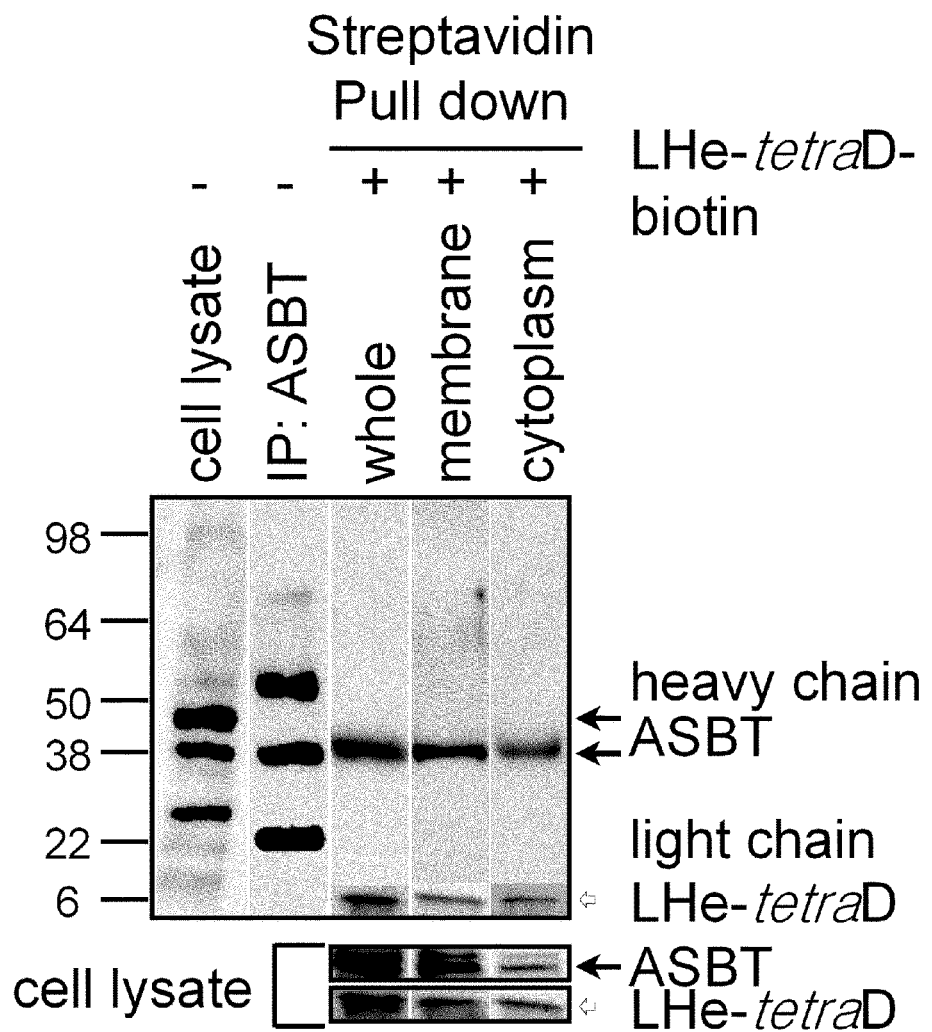

[Fig. 24]
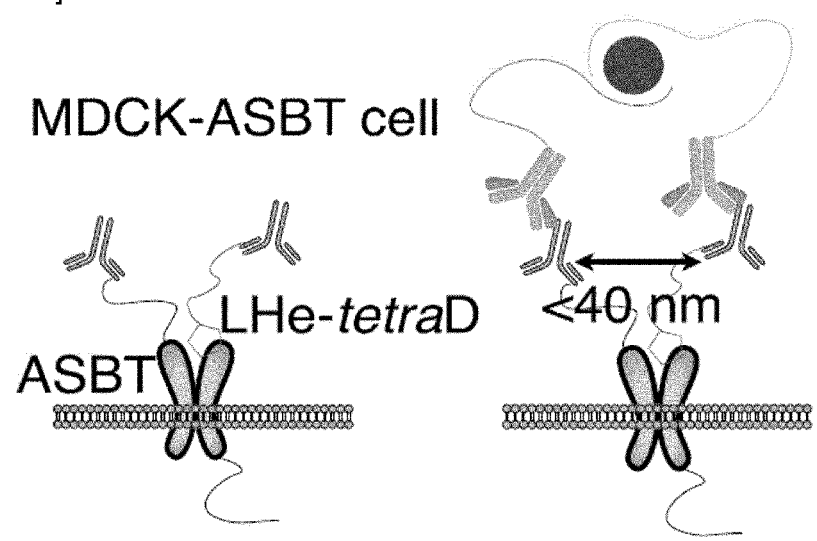
[Fig. 25]
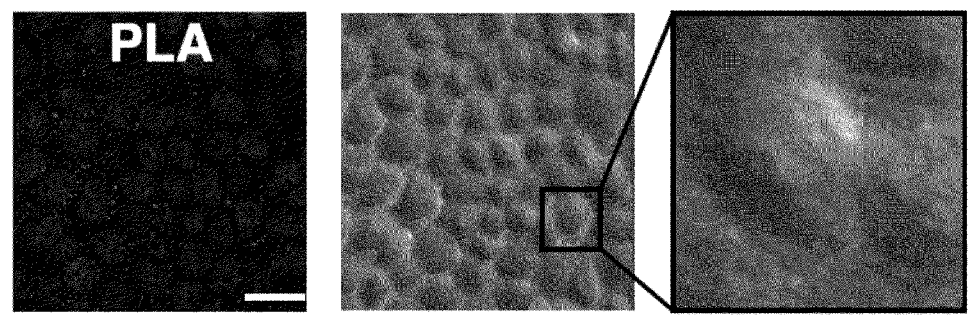

[Fig. 26]
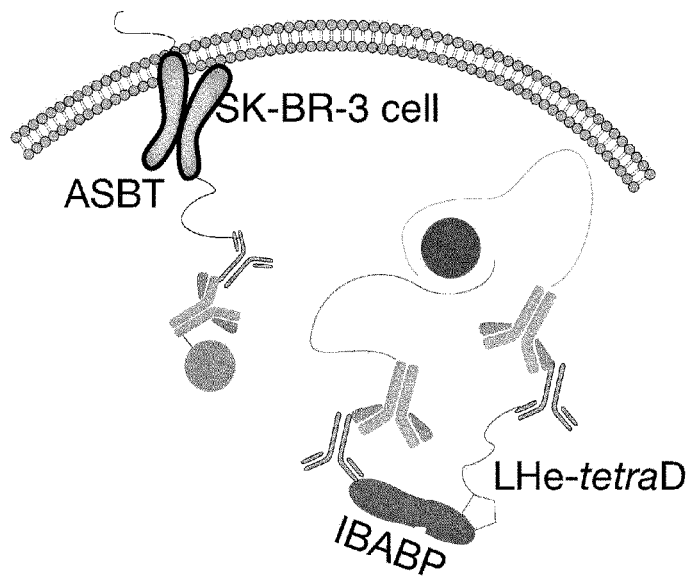
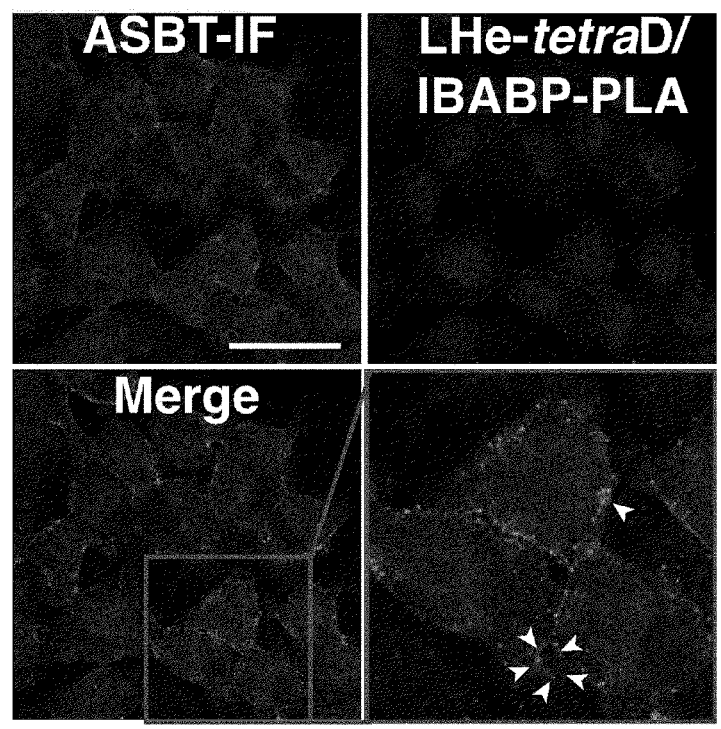

BILE ACID OLIGOMER CONJUGATE FOR NOVEL VESICULAR TRANSPORT AND USE THEREOF

RELATED APPLICATIONS

This application is the U.S. National Stage of International Application. No. PCT/KR2012/010265, filed 29 Nov. 2012, the specification of which is incorporated by reference herein.

TECHNICAL FIELD

The present invention relates to a method for preparing an end site-specific macromolecule-bile acid oligomer conjugate, comprising conjugating a bile acid oligomer which is prepared by oligomerization of two or more bile acid monomers to the terminal site of a macromolecule; a method for body absorption of an end site-specific macromolecule-bile acid oligomer conjugate, comprising administering the macromolecule-bile acid oligomer conjugate prepared by the above method to a subject orally; an end site-specific macromolecule-bile acid oligomer conjugate wherein the bile acid oligomer is conjugated to the terminal site of macromolecule; a composition comprising the conjugate; an oral formulation for macromolecule comprising the conjugate, a solubilizer, an excipient, a disintegrant, a binder, and a lubricant; a pharmaceutical composition comprising a heparin-bile acid oligomer conjugate wherein the bile acid oligomer is conjugated to the terminal site of heparin; and a method for treating thrombosis using said composition.

BACKGROUND ART

A macromolecule refers to a large molecule formed by polymerization of small subunits. It includes polypeptides such as polysaccharide derivatives, and polypeptide such as insulin. Some of the macromolecules such as insulin, exenatide and heparin possess biological activities and are used for therapeutic purposes.

Heparin is a mucopolysaccharide mainly composed of repeating units of D-glucosamine and L-iduronic acid. It is a component found in blood having anti-coagulant activity and has a physiological role such as anti-inflammation and inhibition of angiogenesis. Due to its numerous ionizable sulfate groups, heparin possesses a strong electronegative charge. It is also a relatively strong acid that readily forms water-soluble salts, e.g. heparin sodium. It is found in mast cells and can be extracted from many body organs, particularly those with abundant mast cells. The liver and lungs are especially rich in heparin. The circulating blood contains no heparin except after profound disruption of mast cells. Heparin has many physiological roles, such as blood anticoagulation, inhibition of smooth muscle cell proliferation, immunesuppressive activity, and so forth. In particular, heparin is a strong anti-coagulant agent that interacts strongly with antithrombin III to prevent the formation of fibrin clots. Having these properties, heparin has been used for preventing and treating deep vein thrombosis and pulmonary embolism.

Despite of its physiological usefulness, the application of heparin has been limited due to its large molecular weight and a highly negative charge. These physical characteristics of heparin prevents its absorption through the gastrointestinal (GI) tract, nasal or buccal mucosal layers. Therefore, the only routes of administration available for clinical purposes are intravenous and subcutaneous injections.

Insulin is a macromolecule produced by Langerhans beta cells of pancreas having a distinctive physiological role. It is released from pancreas when the blood glucose level is high in body and regulates the glucose level by allowing higher absoprtion of glucose into liver, muscle, and fat tissue where excess amount of glucose is stored in the form of glycogen, and by inhibiting lipolysis for generating energy source. Having the above functions, insulin has been used for treating diabetics which require regulation of blood glucose level, however due to its large molecular weight it could not be used for oral administration.

Likewise, macromolecules like insulin and heparin which have a specific bioactivity could not be used for oral administration despite of its physiological usefulness. Therefore, there have been many studies for making appropriate formulation for oral administration of macromolecules. In the previous studies on heparin, cationic cell penetrating materials and hydrophilic or hydrophobic detergents have been administered together for better absorption of heparin (Ross & Toth, 2005). In another study, heparin was administered with N-[8-(2-hydroxybenzoyl)amino] caprylate (SNAC), but this method could not be used due to the toxicity of a delivery agent (Berkowitz, et al., 1914-1919). Likewise, inventors of the present application have previously developed a method for oral administration of heparin by improving the the above-mentioned properties of heparin through attaching a type of bile acid such as deoxycholic acid monomer or dimer to heparin in a non-site specific manner(U.S. Pat. No. 6,656,922 and Byun et al., Journal of Control Release 120 (2007) 4-10). However, this method has a limitation in improving the interstinal absorption of heparin because as the number of deoxycholic acid moiety increased for improving absoprtion rate, the anti-coagulant activity of heparin was reduced.

DISCLOSURE OF INVENTION

Technical Problem

In an effort for developing macromolecule-bile acid oligomer conjugate that can improve both of body absorption rate and bioactivity, the present inventors have achieved the present invention by generating a macromolecule conjugated with a bile acid oligomer at its terminal site thereof; utilizing such conjugate for oral administration; and confirming that the bile acid oligomer conjugated to the terminal site of the macromolecule induces intestinal absorption of macromolecules through novel vesicular transport mechanism having a high absorption efficiency.

Solution to Problem

It is an object of the present invention to provide a method for preparing an end site-specific macromolecule-bile acid oligomer conjugate, comprising (a) preparing a bile acid oligomer by oligomerization of two or more bile acid monomers; and (b) conjugating the bile acid oligomer prepared in step (a) to the terminal site of a macromolecule.

It is another obejct of the invention to provide a method of body absorption of end site-specific macromolecule-bile acid oligomer conjugate, comprising (a) preparing a macromolecule-bile acid oligomer conjugate by conjugating a bile acid oligomer that is synthesized by oligomerization of two or more bile acid monomers to the terminal site of macromolecule; (b) administering the conjugate prepared in the step (a) to a subject orally; and (c) transporting the administered conjugate to cytoplasm of the intestinal cell in a form of vesicle by binding to apical sodium bile acid transporter (ASBT) of small-intestinal cell membrane.

It is still another object of the invention to provide macromolecule-bile acid oligomer conjugate, wherein a bile acid oligomer is conjugated to the terminal site of a macromolecule.

It is still another object of the invention to provide a composition comprising the conjugate and a solubilizer, specifically a composition for oral administration.

It is still another object of the invention to provide a pharmaceutical composition comprising a heparin-deoxycholic acid oligomer conjugate.

It is still another object of the invention to provide a method for treating thrombosis by using the pharmaceutical composition.

Advantageous Effects of Invention

The macromolecule-bile acid oligomer conjugate of the present invention has an advantage of high body absorption rate through comprising bile acid oligomer and therefore it can be useful for a development of oral formulation of macromolecule.

BRIEF DESCRIPTION OF DRAWINGS

FIG. 1 is a schematic diagram showing a synthetic process of bisdeoxycholic acid (bisDOCA) which is produced by a reaction of deoxycholic acid with lysine ethyl ester dihydrochloride (2HCl).

FIG. 2 is a schematic diagram showing a synthetic process of N-bisdeoxycholylethylene amine derivative (EtbisDOCA) which is produced by a reaction of bisdeoxycholic acid with ethylene diamine (EDA) through ethoxy ($-OC_2H_5$) group of bisdeoxycholic acid.

FIG. 3 is a schematic diagram showing a synthetic process of the compound ($C_{28}H_{52}N_4O_9$) wherein a lysine monomer is linked with three amine groups by a reaction of Nε—BOC-L-lysine methyl ester hydrochloride with BOC-lysine (BOC)-OSu.

FIG. 4 is a schematic diagram showing a synthetic process of trideoxycholic acid (tri DOCA) which is produced by a reaction of N-hydroxysuccinimide activated Deoxycholic acid (aDOCA) with deprotected lysine monomer.

FIG. 5 is a schematic diagram showing a synthetic process of N-trideoxycholylethyleneamine (EttriDOCA) by a reaction of trideoxycholic acid (tri DOCA) with EDA.

FIG. 6 is a schematic diagram showing a synthetic process of a compound wherein lysine monomer is linked with four amine groups, to be used for a synthesis of tetradeoxycholic acid (tetraDOCA).

FIG. 7 shows a process of preparing tetradeoxycholic acid (tetraDOCA) by a reaction of activated DOCA with deprotected lysine monomer.

FIG. 8 shows a process of synthesizing N-tetradeoxycholylethylene amine (Ettetra DOCA) by a reaction of tetradeoxycholic acid (tetraDOCA) with EDA.

FIG. 9 is a schematic diagram of synthetic process of a representative macromolecule conjugate of the present invention, heparin conjugates, whose terminal site is linked to bile acid oligomer. To be more specific, a reducing 2,5-anhydromannose unit of heparin was reacted with DOCA derivatives to synthesize end site-specific heparin conjugated N-oligodeoxycholylethylamine with addition of sodium cyanoborohydride ($NaCNBH_4$) as a reducing agent.

FIG. 10 shows a common method for synthesizing non-site specific heparin conjugated N-oligodeoxycholylethyl- amine derivatives. Bile acid oligomers such as Et bisDOCA, EttriDOCA, and EttetraDOCA were reacted with heparin through an activation of carboxyl group and 1-Ethyl-3-(3-dimethylaminopropyl)carbodiimide (EDC) of heparin.

FIG. 11 shows the measurement of anti-FXa activity in plasma as a function of time, when an end-site specific heparin-oligomer deoxycholic acid (LHe-oligoDOCA) conjugates, which are the representative end site-specific macromolecule conjugate of the present invention, are administered orally. The conjugates were formulated with lbs and P188 (400 mg/kg and 2.16 mg/kg) and administered to male SD rats. The results demonstrate the difference in absorption profile among the following end site-specific conjugates; (●) LHe-bisDOCA, (□) LHe-triDOCA, (■) LHe-tetraDOCA, (○) LMWH, and (▲) LHe-tetraDOCA which are administered at a dosage of 10 mg/kg each. (▲) LHe-tetraDOCA group was administered with no other treatment (e.g., solubilization) (n=4 rats per group). Results are shown as mean±s.e.m.

FIG. 12 shows the difference in oral absorption profile of non-site specific conjugates based on the analysis of anti-FXa activity of the conjugates in plasma after oral administration of (■) LHm-bisDOCA, (●) LHm-triDOCA, and (□) LHm-tetraDOCA (n=4 rats per group). Results are shown as mean±s.e.m.

FIG. 13 shows the measurement of anti-FXa activity of LHe-tetraDOCA, which is the representative end site-specific macromolecule conjugate of the present invention, when administered at different dosages; (■) 10 mg/kg, (□) 5 mg/kg, or (●) 1 mg/kg. The conjugate was formulated with 1 bs and P188 (400 mg/kg and 2.16 mg/kg) to be orally administered to rats (n=4 rats per group). Results are shown as mean±s.e.m.

FIG. 14 shows the measurements of anti-FXa activity after oral administration of LHe-tetraDOCA, a representative end site-specific macromolecule conjugate of the present invention, in a liquid capsule. Symbol (■) shows the results when administered at a dosage of 5 mg/kg LHe-tetraDOCA and symbol (□) shows the results when orally administered at a dosage of 10 mg/kg LMWH in a capsule (n=4 monkeys per group). Results are shown as means±s.e.m.

FIG. 15 shows the result of Surface Plasmon Resonance (SPR) analysis for LHe-tetra DOCA, which is a representative end site-specific macromolecule conjugate of the present invention. After immobilizing ASBT protein to BlAcore sensor chip, LHe-tetraDOCA was added to determine a dissociation constant (Kd), which are shown in this figure.

FIG. 16 shows the analysis of directional transport of 50 ug/ml LMWH and 50 ug/ml LMWH conjugate wherein oligoDOCA is linked to the terminal site of LMWH. Caco-2 cells were treated with LMWH or LMWH conjugate at 37° C. for 1 h (n=3) and analyzed for the transport of the compound within the cell. FIG. 16A shows an apical region and FIG. 16B shows a basolateral region.

FIG. 17 shows the result of inhibition of apical to basolateral transport of 50 ug/ml LMWH and 50 ug/ml LMWH conjugate wherein oligoDOCA is linked to the terminal site of LMWH by adding 200 μM sodium taurocholate (TCA), an ASBT inhibitor (n=3).

FIG. 18 shows the difference in absorption rates of LMWH conjugates, wherein oligoDOCA is linked to the terminal site of LMWH, depending on the type of oligo DOCA in MDCK-ASBT cells.

FIG. 19 shows the result of LHe-tetraDOCA treatment, which is a representative end site-specific macromolecule conjugate of the present invention, in ASBT-over-expressed MDCK cell and wild-type MDCK cell. The results show that the LHe-tetra DOCA was present inside the ASBT-overexpressed (MDCK-ASBT) cell, indicating that the oral absorption of LHe-tetraDOCA was not derived by an increase hydrophobicity of the compound, but rather is related to an increased affinity toward a bile acid transporter, namely ASBT. Nucleus was stained with DAPI (blue). Scale bar, 10 μm; higher magnification, 5 μm.

FIG. 20 shows the confocal images of the cell confirming the absorption of LHe-tetraDOCA, which is a representative end site-specific macromolecule conjugate of the present invention. Caco-2 cells were treated with RITC-labeled LHe-tetraDOCA and analyzed by a confocal microscope after 30 minutes. The Merge shows that LHe-tetraDOCA is found in the cytoplasm. Tight junctions in the cells were detected by staining with Phalloidin-FITC (green). Nucleus was stained with DAPI (blue). Scale bar, 10 μm; higher magnification, 5 μm.

FIG. 21 shows the western blotting analysis of the cells to determine a spatial distribution of ASBT from cell membrane to cytoplasm after treatment of ASBT-overexpressed MDCK cells with LHe-tetraDOCA. After removal of the compound, ASBT expression was observed in the cell membrane again. Western blotting analysis was done by using goat anti-human ASBT antibody that is specific to ASBT, as well as other antibodies specific for membrane (cadherin), cytoplasm (calnexin), and nucleus (YY1). Also, the results were analyzed comparing Taurocholate (TCA)-treated and untreated groups.

FIG. 22 shows the analysis of the changes in ASBT expression in the MDCK-ASBT cells treated with LHe-tetraDOCA, which is a representative end site-specific macro-molecule conjugate of the present invention, by using a confocal microscope. A cluster of ASBT proteins (green) was absent in the apical membrane after treatment with LHe-tetraDOCA, but re-appeared in the membrane after removal of the compound. The above changes in ASBT expression were not observed in a control group that was not treated with the compound or in a group that was treated with TCA. Scale bar, 20 μm.

FIG. 23 shows the co-immunoprecipation (Co-IP) analysis results for confirming the interaction between LHe-tetraDOCA, which is a representative end site-specific macromolecule conjugate of the present invention, and ASBT in different cell fractions. MDCK-ASBT cells were treated with biotin labeled LHe-tetraDOCA and fractionated into cell membrane and cytoplasm. LHe-tetraDOCA-biotin was pulled down by streptavidin beads and immunoblotted to confirm the interaction. The results demonstrate that ASBT was present in both cell membrane and cytoplasm. <ASBT (upper paenl), LHe-tetraDOCA-biotin, ASBT loading (bottom panel)>.

FIG. 24 shows the result of in-situ PLA (Proximity Ligation Assay) detection analysis for detecting ASBT and LHe-tetraDOCA interaction in MDCK-ASBT cells. The protein interactions are observed as a red mark. The right panel with a higher magnification shows protein interactions in both cell membrane and cytoplasm. Scale bar, 20 μm.

FIG. 25 shows the observation of intracellular transport of ASBT which forms multi-vesicular bodies (MVB) under transmission election microscope (TEM). ASBT was first observed in the cell membrane of MDCK-ASBT cells as indicated by arrow. But the treatment of the cells with LHe-tetraDOCA, which is a representative end site-specific macromolecule conjugate of the present invention, induced changes in cell membrane structure and curvature of the membrane. ASBT was found in the engulfed region of the cell membrane. Afterwards, ASBT in the cell membrane gathered together and were transported near to multi-vesicular bodies (MVB). Small protein transporters including ASBT were fused with MVB. Scale bar, 200 nm.

FIG. 26 shows the results of in-situ PLA demonstrating the interaction between ileal bile acid binding protein (IB-ABP) and LHe-tetraDOCA, which is a representative end site-specific macromolecule conjugate of the present invention, in the SK-BR-3 cells. A mark for interaction between IBABP and LHe-tetraDOCA (red) was observed very close to ASBT mark (green). Also, a higher magnification image showed that these marks have a vesicular structure. Scale bar, 10 μm.

BEST MODE FOR CARRYING OUT THE INVENTION

As one aspect, the present invention provides a method for preparing an end site-specific macromolecule-bile acid oligomer conjugate, comprising (a) preparing a bile acid oligomer by oligomerization of two or more bile acid monomers; and (b) conjugating the bile acid oligomer prepared in step (a) to the terminal site of a macromolecule.

In the present invention, it was confirmed that if a bile acid oligomer that is prepared by oligomerization of two or more bile acid monomers is conjugated to the terminal site of macromolecule, those macromolecules that were hard to be absorbed in intestine can be effectively absorbed into the body through the novel mechanism called vesicular transport by binding to ASBT which is a bile acid transporter in the intestinal cell membrane. Therefore, the present invention provides a method for preparing the end site-specific macromolecule-bile acid oligomer conjugate that can derive effective body absorption of various macromolecules such as polypeptide or polysaccharide through conjugating the bile acid oligomer to the terminal site of macromolecule. The method of the present invention is distinctive in that it does not attach bile acid to a macromolecule step-by-step, but rather it prepares bile acid oligomer separately and attaches it to the terminal site of macromolecule which derives vesicular transport.

As used herein, the term "macromolecule-bile acid oligomer conjugate" refers to a conjugate wherein bile acid oligomer is conjugated with the terminal site of macromolecule. Preferably, macromolecule-bile acid oligomer conjugate of the present invention is characterized in that bile acid oligomer is linked to the terminal site of a macromolecule. That is, the conjugate of the present invention is not formed by conjugating bile acid oligomer to non-specific site of macromolecule or by conjugating the same to the middle-site of a macromolecule. But instead the present conjugate is prepared by end site-specific conjugation of bile acid oligomer with the macromolecule. Since the macromolecule-bile acid oligomer conjugate of the present invention is formed by end site-specific conjugation of bile acid oligomer with the macromolecule, the absorption of the macromolecule is enhanced through the interaction between bild acid oligomer and ASBT of intestinal cells. Furthermore, this form of conjugate does not incur steric hindrance to the site of macromolecule that might be responsible for bioactivity thereof. Therefore, the conjugate of the present invention is advantageous in that it can maintain or improve the bioactivity of a macromolecule, yet still promoting high intestinal absoprtion. Therefore, when the conjugate of the present invention, that is prepared by conjugating bile acid oligomer to the terminal site of macromolecule, is used along with a solubilizer in an oral formulation, it can have a high body absorption rate as well as a strong bioactivity. Among many conjugates of the present invention, heparin-bile acid oligomer conjugate can be formed by conjugating bile acid oligomer specifically to the end site of heparin. Said end site-specific conjugation can be done by reacting a reducing 2,5-anhydromannose unit of heparin at its terminal site with a bile acid derivative such as EtnDOCA (n=bis/tri/tetra), followed by reacting the compound with a reducing agent such as NaCNBH$_4$. Unlike end site-specific conjugate of the present invention, non site-specific heparin-bile acid conjugate is prepared by activating several carboxylic acid groups of heparin and reacting them with bile acid derivatives, thereby conjugating bile acids to the middle site of heparin non-specifically.

The above conjugates, particularly a macromolecule-bile acid tetramer conjugate, is transported into the interior of the intestinal cells in a form of vesicle through binding with apical sodium dependent bile acid transporter or human ileal bile acid transporter (ASBT). Previously, there have been many studies on finding a transport mechanism of bile acids, wherein bile acids pass through ASBT and diffuse into its destination site. In this case, the size of molecule that can pass through ASBT is limited, resulting in low intestinal absorption rate of macromolecule. However, inventors of the present invention recently discovered, for the first time, that if a bile acid oligomer is conjugated to the terminal site of macromolecule, ASBTs form vesicles in the intestinal membrane, inducing vesicular transport, which then lead to intestinal absorption of a macromolecule. Through identifying this novel mechanism, it was suggested, for the first time, that the conjugate of the present invention can be used in an oral formulation that can allow efficient intestinal absorption of macromolecule. Said vesicular formulation can be made by developing a composition of the present conjugate. The present vesicular transport mechanism, wherein macromolecule-bile acid oligomer binds to ASBT and are transported in a vesicular form, was never discovered before.

For the preparation methods of the present invention, the step (a) is for preparing a bile acid oligomer by oligomerization of more than two bile acid monomer.

As used herein, the term "bile acid" means natural and synthetic derivatives of a steroid. For the purpose of the present invention, the type of bile acid is not limited as long as it can be conjugated to a macromolecule in an oligomer form and derive an efficient intestinal absorption. Examples of the bile acid comprises cholic acid, deoxycholic acid, chenodeoxycholic acid, lithocholic acid, ursocholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, or hyodeoxycholic acid. In one embodiment of the present invention, deoxycholic acid was used as a representative bile acid.

As used herein, the term "bile acid oligomer" refers to bile acid derivatives that are prepared by linking more than two bile acid monomers, preferably refers to a derivative formed by linking more than three bild acid monomers, and more preferably refers to a derivative formed by linking more than four bile acid monomers. Preferably, the bile acid oligomer may comprise two to ten bile acid monomers. The bile acid oligomer, that is conjugated to the terminal site of macromolecule of the present invention, binds to ASBT of intestinal cells, which can derive vesicular transport, leading to an efficient intestinal absorption of a macromolecule.

The bile acid oligomer may be composed of more than one type of bile acid which is selected from the group consisting of cholic acid, deoxycholic acid, chenodeoxycholic acid, lithocholic acid, ursocholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid. The bile acid oligomer may comprise the same or different type of bile acids.

In addition, the bile acid oligomer may preferably comprise a linker having a functional group that can be attached to the terminal site of a macromolecule.

As used herein, the term "linker" refers to a linking group that can couple the bile acid oligomer to the terminal site of a macromolecule and may comprise a functional group that can be attached to the terminal site of macromolecule. The functional group that can be coupled to the terminal site of macromolecule can vary depending on the type of a functional group located at the terminal site of macromolecule. For example, in the case of forming a thioesther bond by reacting with thiol group of cysteine residue of protein, maleimide, iodoacetamide, or disulfide group can be used, but is not limited thereto. And in the case of forming a bond through reductive amination with carbonyl group such as aldehyde group or ketone group of polysaccharide, amine group can be used, but not is limited thereto (Kalia J et al., Curr Org Chem. 2010 Jan; 14(2):138-147; Riin Velleste et al., Cellulose, 2010, 17:125-138). Examples of the linker comprise, but are not limited to, alkyl chain, polyethyleneglycol (PEG), pentaethylenehexmaine, 1,5-diamino-2-methylpentane, or ethylenediamine (EDA) with a molecular weight of 300 to 500 Da. In one example of the present invention, EDA was coupled to the synthesized deoxycholic acid oligomer to form a linker comprising amine group. Then, deoxycholic acid oligomer was conjugated to the terminal site of heparin by reacting amine group of the linker attached to the bile acid oligomer with an aldehyde group of reducing 2,5-anhydromannose unit at the end site of heparin. In addition, a linker comprising a maleimide group was attached to deoxycholic acid oligomer, which was then reacted with a thiol group of cysteine residue at the N-terminal site of exenatide in order to produce an end-site specific Exenatide-deoxycholic acid oligomer conjugate.

The preparation methods of the present invention comprises a step (b) of conjugating the bile acid oligomer of step (a) to the terminal site of macromolecule.

As used herein, the term "macromolecule" refers to a large molecule formed by polymerization of small subunits. For the purpose of the present invention, the type of macromolecule is not limited as long as it can be absorbed into intestine through a bile acid oligomer attached at the terminal site thereof. Examples of such macromolecules include, but not limited to, polysaccharide, polypeptide, or polynucleotide. Preferably, the macromolecules refer to polysaccharide, polypeptide, or polynucleotide with a molecular weight larger than 1000 Da.

As used herein, the term "polysaccharide" refers to a macromolecule that is composed of more than two monosaccharides linked by glycoside linkage. Examples of polysaccharides include, but are not limited to, heparin, heparin sodium, sulfonated polysaccharide, cellulose, hydroxymethylcellulose, or hydroxypropylcellulse. The polysaccharide of the present invention is perferably an anti-coagulant polysaccharide, more preferably a heparin.

In addition, the polysaccharide may comprise a carbonyl group at its end site. The polysaccharides comprising a carbonyl group at its end site can be coupled to a bile acid oligomer through a reductive amination reaction with amine group of a linker attached to bile acid oligomer. To be more specific, hydroxyl group at the end site of cellulose can be oxidized to carbonyl group such as ketone, which is then reacted with amine group for coupling (Riin Velleste et al, Cellulose, 2010, 17:125-138). Also, aldehyde group of a reducing 2,5-anhydromannose unit at the terminal of heparin can be coupled to other compound through reacting with an amine group.

As used herein, the term "heparin" refers to an acidic polysaccharide having sulfonic acid group which is mainly composed of repeating units of D-glucosamine and L-iduronic acid. The heparin has an anti-coagulant activity. The heparin used herein includes unfractionated heparin, high molecular weight heparin, low molecular weight heparin (LMWH), heparin fragments and recombined heparin. For a representative heparin-bile acid oligomer conjugate of the present invention which is formed by conjugating bile acid oligomer to the terminal site of heparin, as the number of bile acid moiety combined to heparin increases, the body absorption rate and anti-coagulant activity are both improved, unlike the non-site specific heparin-bile acid oligomer conjugate wherein the bile acid oligomer is attached in the middle of heparin.

As used herein, the term "polypeptide" refers to a amino acid polymer composed of more than 10 amino acid residues linked by peptide bonds, preferably refers to a polypeptide with a molecular weight larger than 1000 Da. Examples of the polypeptide include, but are not limited to, insulin, insulinotropic peptide, or calcitonin. In addition, the insulinotropic peptides include GLP-1, Exendin-3, Exendin-4, as well as agonist, precursors, derivative, fragment, or variant thereof. In one example of the present invention, exenatide, a representative GLP-1 agonist, was used.

Furthermore, the polypeptide may comprise cysteine residue at the N-terminal or C-terminal to be coupled with bile acid oligomer. Cysteine residue of the polypeptide can have a naturally-occurring form or a modified form to be synthetically added to the amino acid sequence (e.g., substitution or addition). The cysteine residue at the N-terminal or C-terminal may be exposed to be conjugated with a bile acid oligomer without a steric hindrance within a sugar structure or tertiary structure among several cysteine residues located in a polypeptide.

Thiol group of cysteine residue located at N-terminal or C-terminal of the polypeptide can be coupled to a bile acid oligomer itself or a functional group of a linker attached to bile acid oligomer. To be more specific, the thiol group can be coulpled to a maleimide group, iodoacetamide group, or disulfide group of a linker attached to bile acid oligomer.

As used herein, the term "terminus" refers to a part of macromolecule where bile acid oligomer can be attached to. For incorporating polypeptide in the conjugate, the terminus may refer to the N- or C-terminus of the polypeptide, and for incorporating polysaccharide in the conjugate, the terminus may refer to monosaccharide located at the end site of polysaccharide, but is not limited thereto.

The conjugate of the present invention prepared using the method of present invention can move to the interior of the intestinal cell through binding with apical sodium dependent bile acid transporter (ASBT), followed by vesicular transport.

The conjugate of the present invention contains bile acid oligomer attached to the terminal site of a macromolecule, which can bind to ASBT and be transported to the interior of the cell in a vesicular transport manner, unlike other previously-known conjugate. The conjugate comprising bile acid oligomer that was transported to interior of the cell by binding to ASBT and vesicular transport then binds to IBABP in cytoplasm and undergoes exocytosis through a basolateral region and ultimately transported to blood circulation. The present vesicular transport mechanism allows intestinal absorption of a macromolecule and thus can be applied for the development of oral formulation.

In one embodiment of the present invention, herapin was used as a representative macromolecule and deoxycholic acid, cholic acid, lithocholic acid and ursodeoxycholic acid were used as bile acid, and deoxycholic acid derivatives were synthesized in a form of oligomer (FIGS. 1 to 8). Using these deoxycholic acid derivatives, heparin-deoxycholic acid oligomer of the present invention wherein deoxycholic acid oligomer is conjugated to the terminal site of herapin was prepared (FIG. 9). Likewise, a representative polypeptide-bile acid oligomer conjugate of the present invention namely, exenatide-deoxycholic acid oligomer conjugate was synthesized, wherein deoxycholic acid oligomer is conjugated to N-terminal of exenatide (Examples 2 and 3). The composition comprising the conjugate of the present invention, wherein deoxycholic acid oligomer is conjugated to the end site of herapin; and a solubilizer was administered to rats and an anti-coagulant activity of the composition was monitored. The results demonstrate that as the number of deoxycholic acid moiety increases the anti-coagulant activity was also significantly increased, unlike a comparative group wherein deoxycholic acid is non-site specifically conjugated. In addition, the anti-coagulant activity was mostly high compared to the comparative group. Especially, when more than trimer of the deoxycholic acid was conjugated to the conjugate, the anti-coagulant activity was significantly higher (FIGS. 11 and 12). Herapin-tetraDOCA (LHe-tetra-DOCA) was used as a representative of end site-specific conjugates of the present invention. When LHe-tetraDOCA was administered to rats at different concentration, anti-coagulant activity of blood was increased (FIG. 13). Likewise, when LHe-tetraDOCA was administered to monkeys, a significantly higher anti-coagulant effect was observed (FIG. 14). The surface plasmon resonance (SPR) was used to analyze the interaction between LHe-tetraDOCA, which is a representative conjugate of the present invention with a high body absorption rate, and ASBT which is a bile acid transporter located in the surface of intestinal cells. SPR analysis results showed $K_D$ of 0.072 µM (FIG. 15). In addition, Caco-2 cells were used as a representative drug delivery system in order to determine a body absorption rate. As a result, the end site-specific conjugates of the present invention showed that as the number of deoxycholic acid moiety combined to the conjugate increased, the transport rate of the conjugate from apical (A) to basolateral (B) region was increased. Especially when deoxycholic acid tetramer was linked to the conjugate, the reverse transport from basolateral to apical region was significantly reduced (FIG. 16). Furthermore, when the transport from apical to basolateral region is inhibited by treating the cell with taucholic acid (TCA), inhibition of transport through ASBT inhibition was more significant for the conjugates comprising deoxycholic acid oligomer, as compared to the conjugates with deoxycholic acid monomer in the present invention. Especially when deoxycholic acid tetramer was linked, the transport of the conjugate was significantly inhibited, indicating that transport via ASBT plays an important role in transport of the conjugate comprising deoxycholic acid oligomer, especially deoxycholic acid tetramer (FIG. 17). These results indicate that a representative heparin-oligoDOCA conjugate of the present invention has a high body absorption rate and anti-coagulant activity. In addition, the present invention identified a transport mechanism for macromolecule conjugate which comprises bile acid oligomer at its terminal site. Furthermore, the present invention demonstrated that the representative conjugate of the present invention LHe-tetraDOCA was located near ASBT in the ASBT-overexpressed cells (FIGS. 19 and 20). And depending on the presence of LHe-tetraDOCA in the cell, ASBT migrated from cell membrane to cytoplasm, or restored back to cell membrane (FIGS. 21 and 22). Also, interaction between ASBT and LHe-tetraDOCA was observed (FIGS. 23 and 24). It was confirmed that through this interaction LHe-tetraDOCA was transported to the interior of the cell through a vesicular transport (FIG. 25). Those transported LHe-tetraDOCA then interacted with IBABP and underwent exocytosis through basolateral region (FIG. 26).

As another aspect, the present invention provides a method of body absorption of an end site-specific macromolecule-bile acid oligomer conjugate, comprising (a) preparing a macromolecule-bile acid oligomer conjugate by conjugating a bile acid oligomer that is synthesized by oligomerization of two or more bile acid monomers to the terminal site of macromolecule; (b) administering the macromolecule-bile acid oligomer conjugate prepared in the step (a) to a subject orally; and (c) transporting the administered macromolecule-bile acid oligomer conjugate to cytoplasm of intestinal cell in a form of vesicle by binding to apical sodium bile acid transporter (ASBT) of small-intestinal cell membrane.

The step (a) is the same as described above.

In the methods of the present invention, the step (b) is an oral administration of the macromolecule-bile acid oligomer conjugate prepared in step (a) to a subject. In the present invention, by conjugating bile acid oligomer to the terminal site of macromolecule, the conjugate comprising macromolecule can be easily absorbed into intestine even by oral administration.

In addition, the above step (c) is a vesicular transport of the administered macromolecule-bile acid oligomer conjugate to interior of intestinal cell by binding to apical sodium bile acid transporter (ASBT) of small-intestinal cell membrane. The present invention identified a new mechanism for macromolecule transport which can be done by binding to ASBT forming vesicles, rather than a diffusion through ASBT transporter. Through this mechanism, those conjugates that were hard to be transported into the cell due to a macromolecule and a large size of the conjugate thereof can now be easily transported into the interior of intestinal cells.

In addition, the method further comprises a step of (d) transporting the conjugate to blood circulation through binding of vesicular-transported conjugate with ileal bile acid binding protein (IBABP) in cytoplasm and undergoing exocytosis to a basolateral region. In the present invention, it was identified that the conjugate binds to IBABP before being exported from vesicles and goes through exocytosis from cytoplasm to blood circulation.

Through this newly identified mechanism, orally administered macromolecule-bile acid oligomer conjugate of the present invention can be easily absorbed to intestine and yet still demonstrating a strong bioactivity within the body system.

As another aspect, the present invention provides an end site-specific macromolecule-bile acid oligomer conjugate, wherein a bile acid oligomer is conjugated to the terminal site of a macromolecule.

The macromolecule, bile acid, bile acid oligomer, and macromolecule-bile acid oligomer conjugate are the same as described above.

As another aspect, the present invention provides the composition comprising the conjugate and solubilizer, more specifically the composition or formulation for oral administration.

The conjugate is the same as described above.

As used herein, the term "solubilizer" refers to an additive to prevent self-aggregation of the conjugate of the present invention. The solubilizer possesses both hydrophilic and hydrophobic molecules thereby preventing self-aggregation of the conjugate of the present invention. Specifically, hydrophilic part of the solubilizer interacts with macromolecule such as heparin while hydrophobic part interacts with bile acid moiety and thus it can reduce the surface tension. Through this action of the solubilizer, bile acid oligomer of the present conjugate can be exposed to and interact with a bile acid transporter, which leads to a higher absorption rate of the conjugate. For the purpose of the present invention, type of the solubilizer is not limited as long as it can facilitate an effective intestinal absorption of the conjugate of the present invention. Examples of the solubilizer include, but are not limited to, polyethylene oxide, hydroxyalkyl cellulose, hydroxypropylalkyl cellulose, polyvinyl alcohol, polyvinylpyrrolidone, copovidone, sodium carboxymethyl cellulose, carbopol, sodium alginate, xanthum gum, locust bean gum, glycofurol, poloxamer, cyclodextrin, or detergent.

The detergents in the present invention can be anionic detergents, non-ionic detergents, zwitterionic detergents, and mixtures thereof. Examples of the detergents include, but are not limited to, alkylallyl-poly (oxyethylene) ethers, alkylallyl formaldehyde condensed poly (oxyethylene) ethers, block copolymers that comprise poly (oxyethylene) as their lipophilic part, poly (oxyethylene) ethers of glycerin esters, poly (oxyethylene) ethers of sorbitan esters, poly (oxyethylene) sorbitan fatty acid esters, polyethylene glycol fatty acid esters, glycerin esters, sorbitan esters, propylene glycol esters, sugar esters, fatty acid alkanol amides, poly (oxyethylene) fatty acid amides, poly (oxyethylene) alkyl amines, polyglycolated glycerides, poly (oxyethylene) castor oils, poly (oxyethylene) hydrogenated castor oils, sorbitan fatty acid esters, monoglycerides of fatty acids, diglycerides of fatty acids, triglycerides of fatty acids, sugar fatty acid esters, bile salts, mixed micelles of bile salts and lecithin, glucose esters, and vitamin E TPGS (D-α-tocopheryl polyethylene glycol 1000 succinate). In addition, examples of the detergents of the present invention include Solutrol HS 15 (Macrogol-15-hydroxystearate); Cremophor RH 40 (Polyoxyl 40 Hydrogenated Castor Oil); Cremophor A6 (Macrogol (6) cetostearyl ether); Cremophor A25 (Macrogol (25) cetostearyl ether); Labrasol (Caprylocaproyl macrogolglycerides (polyoxyglycerides)); Transcutol (Diethylene glycol monoethyl ether); Tweens (Polysorbate 20,21, 40, 61, 65, 80, 81, 85, 120); Poloxamers 124, 188, 237, 338, 407 (Polyoxyethylene polyoxypropylene block copolymer); Nikkol HCO-40 (Polyoxyethylene glycolated natural or hydrogenated castor oil); Myrj 45 (Polyoxyethylene (8) stearate); Tagat L (Polyoxyethylene (30) mono-laurate); Marlosol 1820 (Polyoxyethylene (20) stearate); Marlosol OL 15 (Polyoxyethylene (15) oleate); Brij 52 (Polyoxyethylene (2) cetyl alcohol); Brij 96 (Polyoxyethylene (10) oleyl ether); Brij 700 (Polyoxyethylene (100) stearyl alcohol); Volpo 015 (Polyoxyethylene (15) oleyl ether); Marlowet OA30 (Polyoxyethylene (30) oleyl ether); Marlowet LMA 20 (Polyoxyethylene (20) oleyl ether); Syperonic PE L44

(Polyoxyethylene-polyoxypropylene copolymer); Sypernoic F127 (Polyoxyethylene-polyoxypropylene copolymer); Labrafil M1994CS (Oleoyl macroglycerides (polyoxyglycerides)); Labrafil M2125CS (Linoleyl macroglycerides (polyoxyglycerides)); Labrafac PG (Propylene glycol dicaprylocaprate); Imbitor (Caprylic acid/capric acid mono- and di-glyceride); sorbitan mono stearate; sorbitan tri-stearate; sorbitan mono-oleate; polyethylene glycol mono-oleate; Miglyol 840 (propylene glycol dicaprylate); Gelucire 44/14 (Lauroyl macrogolglycerides (polyoxyglycerides)); Gelucire 50/13 (Stearoyl macrogolglycerides (polyoxyglycerides)); Plurol oleique CC 497 (Polyglyceryl oleate); Lauroglycol FCC (Propylene Glycol Laurate); Capryol PGMC (Propylene glycol caprylate); Lauroglycol 90 (Propylene glycol monolaurate); Capryol 90 (Propylene glycol monocaprylate); fatty acid salts; a-sulfonyl fatty acid esters; Linear alkyl benzene sulfonic acid salts; alkyl sulfonic acid ester salts; alkyl ether sulfonic acid ester salts; alpha olefin sulfonic acid salts; alkyl sulfonic acid salts; sodium lauryl sulfate; alkyl amino fatty acid salts; alkyl betaines; lecithins; lauryl di-methyl betaines; and mixtures thereof.

Furthermore, if the above composition is to be used as a pharmaceutical composition, the composition may further comprise a carrier, excipient (fillers), or diluent suitable for the pharmaceutical formulations. Types of a solid formulation for oral administration include tablets, pills, powders, granules, and capsules. And these solid formulations are prepared by mixing at least one or more excipient with more than one compounds. Examples of such excipient include a saccharides such as lactose, dextrose, sucrose, sorbitol, mannitol, xylitol, erythritol, and maltitol; a starch such as corn starch, wheat starch, rice starch, potato starch; a cellulose such as cellulose, methyl cellulose, sodium carboxymethyl cellulose and hydroxypropyl methylcellulose; and a filler such as gelatin and polyvinyl pyrrolidone. In some cases, crosslinked polyvinylpyrrolidone, agar, alginic acid or sodium alginate may be added as a disintegrant. Furthermore, the pharmaceutical composition of the present invention may additionally comprise a lubricant, a humectant, an aromatic, an emulsifier, and a preservative such as anti-coagulants, magnesium stearate, talc. Types of liquid formulation for oral administration include a suspension concentrate, a solution, an emulsion, and a syrup. And these liquid formulations may comprise a simple diluent such as water and liquid paraffin as well as various excipients such as a humectant, a flavor, an aromatic, and a preservative.

Additionally, if the composition of the present invention is a pharamceutical composition, it may be administered in a pharmaceutically effective amount.

As used herein, the term "pharmaceutically effective amount" refers to an amount sufficient for the prevention or treatment of diseases, which is commensurate with a reasonable benefit/risk ratio applicable for medical treatment. An effective dosage of the present composition may be determined depending on the subject and severity of the disease, age, gender, type of disease, drug activity, sensitivity towards drug, administration time, administration routes, excretion rates, duration of treatment, simultaneously used drugs, and other factors known in medicine. The composition of the present invention can be administered as an individual medicine or co-administered with other medicines either successively or concurrently. And it can be administered as a single dose or multiple doses. Considering the above factors, it is important to administer a minimum amount that can yield the maximum effect without side effects, which can be easily determined by those skilled in the art.

In one example of the present invention, it was confirmed that the composition comprising the heparin-oligoDOCA conjugate of the present invention and a solubilizer demonstrates a higher anti-coagulant activity, compared to the composition comprising the non-site specific heparin-oligoDOCA conjugate and a solubilizer (Tables 2 and 3). Difference in anti-coagulant activities among the conjugates became more apparent as the number of deoxycholic acid moiety in the conjugate increased, and especially heparin-tetraDOCA conjugate having deoxycholic acid tetramer showed a significantly higher oral absorption rate and anti-coagulant activity.

As another aspect, the present invention provides a formulation for oral administration of a macromolecule, comprising the conjugate; solubilizer; excipient; disintegrant; binder; and lubricant.

The present formulation for oral administration of macromolecule comprises the conjugate of the present invention and thereby allowing easier intestinal absorption when orally administered. Also, since the formulation comprises the bile acid oligomer at the terminal site of macromolecule, the physiological activity of the macromolecule can still be maintained or increased.

As another aspect, the present invention provides a pharmaceutical composition comprising the herapin-bile acid oligomer conjugate.

Said heparin-bile acid oligomer conjugate is the same as described above. Also, the pharmaceutical composition may comprise solubilizer, which can enhance oral absorption of the conjugate.

The pharmaceutical composition comprises the heparin-bile acid oligomer conjugate, and therefore it can treat human diseases that can be treated by heparin, for example, cancer, inflammatory disease such as arthritis, or thrombosis.

As used herein, the term "cancer" refers to a cancer that can be treated by the composition. Examples of such cancer include, but are not limited to, esophageal cancer, stomach cancer, colorectal cancer, rectal cancer, oral cancer, pharynx cancer, laryngeal cancer, lung cancer, colon cancer, breast cancer, cervical cancer, endometrial cancer, ovarian cancer, prostate cancer, testicular cancer, gallbladder cancer, liver cancer, pancreatic cancer, bone cancer, connective tissue cancer, skin cancer, brain cancer, thyroid cancer, acute leukemia, chronic leukemia, Hodgkin disease, lymphoma, or multiple myeloma. Since heparin is known to induce cancer cell death (Robert J Linhardt et al., Chem Biol. 2004 Apr;11(4):420-2.), the heparin-bile acid oligomer conjugate of the present invention can be effectively used for preventing or treating cancer with an improved body absorption rate and an active bioactivity of heparin.

As used herein, the term "inflammatory disease" refers to a disease caused by inflammation. For the purpose of the present invention, it may refer to any inflammatory disease that can be treated by heparin. Examples of the inflammatory disease include arthritis, rheumatic arthritis, allergy, plasmacitosis, hyperimmunoglobulinemia, anemia, nephritis, cachexia, disease prominent to livestock farmers, blood-vessel proliferative nephritis, multiple sclerosis, uveitis, chronic thyroiditis, chronic delayed hypersensitivity, contact dermatitis, systemic erythematous, Crohn's disease, psoriasis, juvenile idiopathic kraurosis, diabetic, or Alzheimer's disease, but are not limited thereto.

As used herein, the term "thrombosis" refers to a disease caused by coagulation of blood in a blood vessel. The thrombosis can lead to a development of acute cardiac infarction, stroke, pulmonary embolism, acute peripheral arterial occlusion, deep venous thrombosis, portal vein thrombosis, acute renal vein occlusion, cerebral venous sinus thrombosis, or central retinal vein occlusion.

As used herein, the term "prevention" refers to all of the actions in which the symptoms of thrombosis are restrained or the occurrence of thrombosis is retarded by administration of the composition, and the term "treatment" refers to all of the actions in which the symptoms of thrombosis are relieved by administration of the composition.

In addition, the composition can be administered in a pharmaceutically effective amount, which is the same as described above.

As another aspect, the present invention provides a method for treating thrombosis, comprising administering the composition comprising the heparin-bile acid oligomer conjugate to the subject suspected of thrombosis.

Said heparin-bile acid oligomer conjugate, composition, and thrombosis are the same as described above.

To be more specific, the treatment method of the present invention comprises administration of the composition in pharmaceutically effective amount to the subjects suspected of thrombosis. The subjects refer to mammals including, but not limited to, dog, cow, horse, rabbit, mouse, rat, chicken, and human. For the purpose of the present invention, the composition can preferably be administered orally and the appropriate dosage varies depending on the condition and weight of the subjects, severity of disease, drug type, administration route and duration. Appropriate dosage can be determined properly by those skilled in the art.

MODE FOR THE INVENTION

The present invention is described in more details through providing Examples as below. However these Examples are merely meant to illustrate, but in no way to limit, the claimed invention.

Example 1

Synthesis of Bile Acid Oligomer

Example 1-1

Synthesis of a DOCA Dimer

A dimer of deoxycholic acid (bisDOCA) was synthesized by using L-lysine ethyl ester.

To be more specific, 6.6 g (16.85 mmol) deoxycholic acid dissolved in 300 ml THF solution was purged with nitrogen and incubated in ice bath for 30 min, followed by a reaction with 4-methylmorpholine and ethylchloroformate at room temperature for 4 hours. Completion of the reaction was confirmed by thin layer chromatography (TLC). And 2.08 g (8.43 mmol) L-lysine ethyl ester dihydrochloride was added to the reaction which was then refluxed overnight at a temperature in a range of 70 to 80° C. After overnight refluxing, the precipitate was collected by filtering and dried further by letting the solvent evaporates. The crude precipitate was re-dissolved in chloroform and washed by using 5% HCl, 10% NaOH, and distilled water successively. The organic layer was added with sodium sulfate to remove aqueous solution and filtered away from the sodium sulfate, and then concentrated down by evaporating solvent. The concentrate was purified by running it through a column chromatography using 0.04-0.06 mm silica gel and an eluent of 10% Methanol in Dichloromethane. The collected fractions of final product were combined, purified, and recrystallized in a cold ether solution. The overall reaction process is shown as a schematic diagram in FIG. 1.

As a next step, the obtained DOCA dimer (14.4 mmol) was dissolved in 108.54 ml anhydrous ethanol (108.54 ml) and was added drop wise with 96.06 ml (1.44 mol) ethylenediamine (EDA) in a cooled beaker. Then the reaction mixture in the beaker was purged with nitrogen and left in the dark for 3 days. The remaining solvent and excess amount of ethylenediamine were evaporated through vacuum and the compound was precipitated in a cold water. The final product was purified by running it through adsorption chomatography using 0.04-0.063 mm silica gel and a solution of chloroform, methanol and ammonium hydroxided mixed in a ratio from 7.75:3:0.25 to 5:5.75:0.25 as an eluent. The characteristics of the final product were analyzed by $^1$H NMR, elemental analysis, IR, MALDI-TOF, and LC/MS (Agilent 1100 series). For LC/MS analysis, ESI mass spectra was used along with Xterra phenyl (150×2.1, 3.5 μm) column. The overall reaction process is shown as a schematic diagram in FIG. 2.

Example 1-2

Synthesis of DOCA Trimer

A lysine monomer BOC—CH$_3$O-lys(lys(boc)$_2$) containing three amino groups was prepared by a method of peptide synthesis. The first reagent H-lysBOC—CH$_3$O.HCl [GL Biochem, China] (1.9 g, 6.4 mmol) was dissolved in 11.67 ml DMF under sonication. Then the solution was added with 2.82 ml (25.6 mmol) 4-methyl morpholine dropwise, followed by addition of 2.5 ml methanol (HPLC grade). The mixed solution was stirred for 60 minutes in order to remove HCl salt. Meanwhile, the second reagent BOC-lysBOC—OSu [Sigma] (2.897 g, 6.4 mmol) was dissolved in 10.99 ml DMF and cooled down. The solution was purged with nitrogen gas and left in the dark overnight. After overnight reaction, the solvent was completely removed through evaporation under vaccum. The crude product was re-dissolved in 60 ml chloroform and washed by using 20 mL of 5% HCl and 20 ml distilled water successively. After evaporating the solvent the crude product was dissolved in methanol and precipitated in a cold distilled water. The precipitate was isolated by centrifugation and freeze-dried to remove water in the compound. The overall reaction process is shown as a schematic diagram in FIG. 3.

As a next step, the BOC groups were removed by a commonly used BOC deprotection method.

First, 8.16 ml (115.52 mmol) acetyl chloride and 114.48 ml methanol were mixed by stirring for 60 minutes and the mixed solution was cooled down. Then 3.4 g (5.775 mmol) BOC—CH$_3$O-lys(lys(boc)$_2$) was added to the above solution and stirred for 12 h in ice bath. After removing all the solevent, the compound was re-dissolved in distilled water. The dissolved compound in water was washed with chloroform. After liquid extraction, chloroform was removed yielding the aqueous layer in the flask, which was then freeze-dried to obtain the final product. The reaction process is shown as a schematic diagram in FIG. 4.

The above synthesized lysine monomer (500 mg, 1.257 mmol) was dissolved in 15 ml DMF using sonication. In order to remove HCL salt, 4-methyl morpholine (1.243 ml, 11.3 mmol) was added slowly. After 40 to 50 minutes of stirring, the solution was cooled down by putting it in ice bath. To this cooled solution, N-hydroxysuccinimide activated deoxycholic acid (2.68 g, 5.658 mmol) dissolved in 12.55 ml DMF was added dropwise. The mixed solution was purged with nitrogen for 24 hours and stirred in the dark. The solvent was removed the next day and the resulting compound was precipitated in a cold distilled water. The precipitate was filtered and vaccum-dried to obtain the final product. The final product was further purified and analyzed by the method described in Example 1-1.

Example 1-3

Synthesis of DOCA Tetramer

Lysine monomer BOC—CH$_3$O-lys(lys(boc)$_2$) was prepared by the method described in Example 1-2 and then was converted to BOC-lys(lys(boc)$_2$)-COONa by saponification at 70° C. for 6 hours using sodium hydroxide. Then the resulting compound was acidified by adding 1N HCl and turned into BOC—COOH-lys(lys(boc)$_2$). The acidified lysine monomer was then dissolved in DMF mixed with DCC and N-hydroxysuccinimide in ice bath and stirred at 4° C. for 30 minutes. The precipitated DCU was removed by filtration and finally the compound A was obtained.

As a next step, H-lysBOC—CH$_3$O.HCl was mixed with 4-methyl morpholine and stirred for 1 hour yeilding compound B. Compound A was slowly added to compound B and stirred for 24 hours to prepare Lysine dimer BOC—CH$_3$O-lys(lys(boc)$_2$)$_2$. The precipitated DCU was removed by filtration. The solvent was removed by evaporation under vacuum and the compound was precipitated in a cold distilled water. The crude product was re-dissolved in methanol and precipitated. Then the purified product BOC—CH$_3$Olys(lys(boc)$_2$)$_2$ was freeze-dried to remove remainning water molecules. As described in Example 1-2, the same BOC deprotection method was used to remove BOC group from BOC—CH$_3$O-lys(lys(boc)$_2$)$_2$. Then a lysine dimer containing four amino groups was synthesized.

The synthesized lysine dimer was reacted with N-hydroxysuccinimide activated deoxycholic acid (aDOCA) to synthesize deoxycholic acid (DOCA) tetramer by the same method described in Example 1-2 except for the molar ratio of reagents. The synthesized DOCA tetramer was further purified and analyzed by the same method described in Example 1-2.

Example 1-4

Synthesis of Cholic Acid Oligomer

A dimer, trimer, and tetramer of cholic acid were prepared using cholic acid moiety by the same method described in Example 1-1 to 1-3.

Example 1-5

Synthesis of Ursodeoxycholic Acid Oligomer

A dimer, trimer, and tetramer of ursodeoxycholic acid were prepared using ursodeoxycholic acid moiety by the same method described in Example 1-1 to 1-3.

Example 1-6

Synthesis of Lithocholic Acid Oligomer

A dimer, trimer, and tetramer of lithocholic acid were prepared using lithocholic acid moiety by the same method described in Example 1-1 to 1-3.

Example 2

Synthesis of End Site-Specific Heparin-oligoDOCA Conjugates

FIG. 9 shows a schematic of synthetic process of the conjugate of the present invention that was formed by conjugating of deoxycholic acid oligomer to the terminal site of heparine. Details of the process are described below.

Example 2-1

Synthesis of End Site-Specific Heparin-bisDOCA Conjugate (LHe-bisDOCA)

The 35 mg (7 μM) heparin was dissolved in a mixture of formamide and DMF (1.5:1.0 v/v) with low heating and added with sodium cyanoborohydride (77.65 μM). Then bisDOCA was added to heparin dissolved in FA/DMF solution in a ratio of 1:12 and the mixture was stirred at 50° C. for 21 hours. Imine bond formed afer the above reaction was reduced by adding sodium cyanoborohydride. The synthesized product was precipitated and purified by adding a cold ethanol to the reaction mixture three times. After the last purification process, the solvent was completely evaporated, then the remaining compound was freeze-dried to obtai the final product LHe-bisDOCA in a powder form. The synthezied conjugate was confirmed by the analysis method described in Example 1.

Example 2-2

Synthesis of End Site-Specific Heparin-triDOCA Conjugate (LHe-triDOCA)

End site-specific heparin-triDOCA was synthesized and analyzed by the method described in Example 2-1 using deoxycholic aid trimer (EttriDOCA) of Example 1-2.

Example 2-3

Synthesis of End Site-Specific Heparin-tetraDOCA Conjugate (LHe-tetraDOCA)

End site-specific heparin-tetraDOCA was synthesized and analyzed by the method described in Example 2-1 using deoxycholic acid tetramer (EttetraDOCA) of Example 1-3.

Example 3

Synthesis of Exenatide-tetraDOCA Conjugate (tetraDOCA-6M-exenatide)

Exenatide which is a representative example of GLP-1 agonist was conjugated to bile acid oligomer at its terminal site to synthesize tetraDOCA-6M-exenatide as described below.

First, 30 mg of tetraDOCA was dissolved in 0.75 ml DMF and reacted with 9.5 mg linker 6-maleimidohexanoic NHS dissolved in 0.75 ml DMF. As a reaction catalyst, 4 μl triethylamine was added to the reaction mixture which were then stirred for 1 hour at room temperature. The reaction product was purified by HPLC process using methanol as mobile phase. The synthesized and purified linker-tetraDOCA, which comprises the maleimide group, was isolated by fraction collector and freeze-dried.

For the reaction with linker-tetraDOCA, exenatide was modified by substituting serine residue at the N-terminal of exenatide with cysteine. First, 2 mg of modified exenatide and 5.1 mg linker-tetraDOCA compound containing maleimide group were dissolved in minimal amount of DMF and reacted for 24 hours at a room temperature. Purification of the reaction product was done by HPLC process using methanol as a mobile phase in a gradient from 5% to 60% to 95% at 5 minutes, 20 minutes, and 40 minutes of HPLC. The velocity of mobile phase in HPLC was 1 ml/min, and compound peak was measured through UV/vis at a wavelength of 227 nm. The synthesized and purified linker-tetraDOCA was isolated by fraction collector and freeze-dried.

Example 4

Synthesis of GLP-1-bile Acid Oligomer Conjugate

GLP-1 was used instead of exenatide to prepare GLP-1-bile acid oligomer conjugate by the same method described in Example 3.

Example 5

Synthesis of Exendin-3-bile Acid Oligomer Conjugate

Exendin-3 was used instead of exenatide to prepare Exendin-3-bile acid oligomer conjugate by the same method described in Example 3.

Example 6

Synthesis of Exendin-4-bile Acid Oligomer Conjugate

Exendin-3 was used instead of exenatide to prepare Exendin-4-bile acid oligomer conjugate by the same method described in Example 3.

Comparative Examples

Synthesis of Non-Site Specific Heparin-OligoDOCA Conjugate

FIG. 10 shows a schematic for preparation of the conjugate that was formed by conjugating of deoxycholic acid oligomer to heparin in a non-site specific manner. Detailed synthetic process is described below.

Comparative Example 1

Synthesis of Non-Site Specific Heparin-bisDOCA Conjugate (LHm-bisDOCA)

Non-site specific heparin-bisDOCA conjugates were prepared by conjugating of heparin with N-bisdeoxycholylethyl amine (EtbisDOCA) in nonequivalent molar ratio.

To be more specific, 100 mg low molecular weight Heparin (LMWH) was dissolved in 3.125 ml formamide solution with low heating. The carboxylic acid group of heparin was activated by adding EDAC. Then the activated heparin was reacted with EtbisDOCA in a molar ratio ranging from 1:1.2 to 1:12 at 4° C. for 12 hours. The resulting compound was precipitated in a cold ethanol, purified by filtration, and vaccum-dried. The heparin conjugate was re-dissolved in a distilled water and freeze-dried to be in a powder form.

Table 1 delineates the conjugated form of LMWH-bisDOCA, namely LHm-bisDOCA, according to the coupling rate of bisDOCA. A coupling rate of DOCA dimer (bisDOCA) with LMWH was determined by a gasometric method which was calibrated with sulfuric acid [A. Fini et al Journal of Pharmaceutical sciences 81 (1992) 726-730]. Anti-coagulant activity of non-site specific LH-bisDOCA conjugates was determined by using anti-FXa Chomagenic assay kit based on the anti-FXa activity of heparin.

Comparative Example 2

Synthesis of Non-Site Specific Heparin-triDOCA Conjugate (LHm-triDOCA)

Non-site specific heparin-triDOCA conjugates (LHm-triDOCA) were prepared by conjugating of heparin with N-trideoxycholylethyleneamine in a nonequivalent molar ratio by the method described in Comparative Example 1. A coupling rate and anti-coagulant activity of heparin-triDOCA conjugates (LHm-triDOCA) were determined by the method described in Comparative Example 1.

Comparative Example 3

Synthesis of Non-Site Specific Heparin-tetraDOCA Conjugate (LHm-tetraD)

Non-site specific heparin-tetraDOCA conjugates (LHm-tetraD) were prepared by conjugating of heparin with N-tetradeoxycholylethyleneamine in a nonequivalent molar ratio by the method described in Comparative Example 1.

Experimental Example 1

Analysis of Characteristics of Heparin-oligoDOCA Conjugates (LH-oligoDOCA)

Heparin-oligoDOCA conjugates were analyzed by Infrared Radiation (IR) spectroscopy and Proton Nuclear Magnetic Resonance ($^1$H NMR) Spectroscopy to confirm the presence of a specific amide bond and peaks for bile acids. Further, end site-specific heparin-oligoDOCA conjugates were analyzed by using $^1$H-$^1$H COSY and $^{13}$C NMR. Anti-coagulant activity of the synthesized heparin conjugates was analyzed based on the compound's reactivity to FXa by measuring the absorption at 405 nm using Anti-FXa Chomagenic assay kit.

Aggregation of the above conjugates was monitored at 633 nm and 25±1° C. by Electrophoretic Light Scattering (ELS-800). The synthesized conjugates were mixed with labrasol and P188 for complete dissolving. Self-aggregation was normally detected at a concentration of 1 mg/ml. The solubility of each conjugate was determined as a concentration that no longer causes aggregation after performing a serial dilution of the sample.

TABLE 1

| LMWH-oligo deoxycholic conjugates | Synthetic Derivatives | Relative activity* (IU/mg) | Conjugation ratio* | Partition Coefficient (o/w) * | Solubility (mg/ml) |
|---|---|---|---|---|---|
| LMWH | Fraxiparin | 100 | — | 0.01 ± 0.01 | — |
| Non-specific surface conjugated derivatives | LHbisD | 83.0 ± 2.1 | 0.8 ± 0.0 | 0.22 ± 0.01 | 0.75 |
|  | LHtriD | 74.9 ± 1.2 | 1.0 ± 0.1 | 0.27 ± 0.03 | 0.25 |
|  | LHtetraD | 46.3 ± 3.2 | 1.0 ± 0.1 | 0.35 ± 0.05 | 0.125 |
| Specific end site conjugated derivatives | EHbisD | 93.1 ± 1.9 | 1.4 ± 0.1 | 0.19 ± 0.01 | 0.156 |
|  | EHtriD | 98.6 ± 2.1 | 0.9 ± 0.0 | 0.26 ± 0.01 | 0.0625 |
|  | EHtetraD | 96.5 ± 1.2 | 0.8 ± 0.0 | 0.33 ± 0.01 | 0.0625 |

Experimental Example 2

In Vivo Study on Oral Absorption of Heparin-oligoDOCA Conjugates

In order to determine the absorption rate of the formulation containing end site-specific heparin-oligoDOCA conjugate through the small intestine where bile acid transporters are located, anti-coagulant activity of heparin conjugate was measured based on the anti-FXa activity of heparin.

For end site-specific heparin-oligoDOCA conjugate, the conjugate was formulized with a solubilizers 1 bs (400 mg/kg) and P188 (2.16 mg/kg) and administered at a dosage of 10 mg/kg to male rats.

As a result, compared to the control sample, as the number of the combined deoxycholic acid moiety increased, the anti-coagulant activity of the conjugate was increased as well. Especially the heparin conjugate containing deoxycholic acid tetramer showed a significantly higher anti-coagulant activity compared to the ones containing dimer or trimer of deoxycholic acid (FIG. 11). On the other hand, for the non-site specific conjugates, ones containing dimer of deoxycholic acid showed the highest anti-coagulant activity (FIG. 12).

These results demonstrate that the end site-specific heparin-oligoDOCA conjugates have a higher absorption rate and anti-coagulant activity, compared to non-site specific conjugates.

In addition, LHe-tetraDOCA was orally admnistered at various dosages to SD rats (FIG. 13). Samples of LHe-tetraDOCA at different dosages were formulized with Polxamer 188 and Labrasol. As shown in FIG. 13, LHe-tetraDOCA has a concentration-dependent anti-coagulant activity.

Also, different formulations were prepared by combining conjugates with different solubilizers and orally administered to SD rats. Then the plasma concentration of the administered sample was measured pharmadynamically.

Compositions of each formulation used are listed in Table 2. And the total volume of 400 μl was prepared for each formulation to be orally administered.

TABLE 2

| Material | | Amount (mg per kg body weight) |
|---|---|---|
| Comparative Formulation 1 | LMWH | 10 |
| Comparative Formulation 2 | LHbisD | 10 |
| Formulation 3 | LHbisD + sodium lauryl sulfate | 10 + 0.036 |
| Formulation 4 | LHbisD + Labrasol | 10 + 200 |
| Formulation 5 | LHbisD + Palmitic acid | 10 + 1 |
| Formulation 6 | LHbisD + Myristic acid | 10 + 1 |
| Formulation 7 | LHbisD + P407 | 10 + 1 |
| Formulation 8 | LHbisD + P188 | 10 + 1 |
| Comparative Formulation 9 | LMWH + P188 + Labrasol | 10 + 2 + 200 |
| Formulation 10 | LHbisD + P188 + Labrasol | 10 + 2 + 200 |
| Formulation 11 | LHtriD + P188 + Labrasol | 10 + 2 + 200 |
| Formulation 12 | LHtetraD + P188 + Labrasol | 10 + 2 + 200 |
| Formulation 13 | EHbD + P188 + Labrasol | 10 + 2 + 200 |
| Formulation 14 | EHtriD + P188 + Labrasol | 10 + 2 + 200 |
| Formulation 15 | EHtetraD + P188 + Labrasol | 10 + 2 + 200 |
| Comparative Formulation 16 | EHtetraD | 10 |
| Comparative Formulation 17 | EHtetraD + P188 + Labrasol | 5 + 2 + 200 |
| Comparative Formulation 18 | EHtetraD + P188 + Labrasol | 1 + 2 + 200 |

Furthermore, after oral administration of formulations listed in Table 2, their plasma concentration was analyzed pharmadynamically and the results are shown in Table 3.

TABLE 3

| | $EAUC_{0-8h}$ (IU * h/ml) | $E_{max}$ (IU/ml) | $T_{max}$ (h) |
|---|---|---|---|
| Comparative Formulation 1 | 0.26 ± 0.05 | 0.07 ± 0.01 | 0.62 ± 0.25 |
| Comparative Formulation 2 | 0.79 ± 0.19 | 0.25 ± 0.1 | 1.0 ± 0.7 |
| Formulation 3 | 0.84 ± 0.4 | 0.21 ± 0.07 | 0.87 ± 0.25 |
| Formulation 4 | 2.03 ± 0.07 | 0.65 ± 0.23 | 0.75 ± 0.35 |
| Formulation 5 | 0.63 ± 0.05 | 0.21 ± 0.01 | 1.25 ± 1.06 |
| Formulation 6 | 0.62 ± 0.08 | 0.25 ± 0.06 | 0.75 ± 0.35 |
| Formulation 7 | 2.34 ± 0.61 | 0.64 ± 0.29 | 1.5 ± 0.57 |
| Formulation 8 | 2.55 ± 0.37 | 0.68 ± 0.07 | 1.12 ± 0.63 |
| Comparative Formulation 9 | 0.68 ± 0.2 | 0.34 ± 0.16 | 1.33 ± 0.58 |
| Formulation 10 | 2.2 ± 0.32 | 0.61 ± 0.11 | 0.87 ± 0.06 |
| Formulation 11 | 0.92 ± 0.31 | 0.24 ± 0.1 | 0.5 ± 0.0 |
| Formulation 12 | 1.47 ± 0.16 | 0.36 ± 0.02 | 0.5 ± 0.0 |
| Formulation 13 | 2.22 ± 1.4 | 0.62 ± 0.3 | 7.25 ± 0.5 |
| Formulation 14 | 2.01 ± 0.38 | 0.57 ± 0.03 | 0.67 ± 0.29 |
| Formulation 15 | 2.81 ± 0.37 | 1.04 ± 0.07 | 0.5 ± 0.0 |
| Comparative Formulation 16 | 1.02 ± 0.22 | 0.21 ± 0.04 | 2 ± 1 |
| Comparative Formulation 17 | 1.54 ± 0.23 | 0.44 ± 0.19 | 0.33 ± 0.14 |
| Comparative Formulation 18 | 0.56 ± 0.15 | 0.22 ± 0.05 | 0.44 ± 0.1 |

In Table 3, EAUC indicates the area under the concentration vs. time graph from a time point 0 to 8 hours. $E_{max}$ indicates the concentration causing maximum effect and $T_{max}$ indicates required time to reach the concentration that causes maximum effect.

As shown in Table 3, Comparative Formulation 2, that contained heparin-bisDOCA conjugate (LH-bisDOCA) without solubilizer, had a higher absorption rate when administered orally, compared to Comparative Formulation 1 that contained LMWH-bisDOCA. When solubilizer Labrasol, Poloxamer 188 or Poloxamer 407 was added to LMWH-bisDOCA (Formulations 4, 7, 8 respectively), the absorption rate was increased even more.

Also, among the formulations that contained both of solubilizers (P188 and Labrasol) and heparin-oligoDOCA conjugate, formulations with site-specific heparin-oligoDOCA conjugate, especially ones with trimer or tetramer of deoxycholic acid (Et triDOCA or EttetraDOCA), showed a higher oral absorption rate and anti-coagulant activity compared to the formulations containing non-site specific heparin-oligoDOCA conjugate (Formulations 10 to 12). Unlike non-site specific conjugates, the site-specific ones showed an increasing oral absorption rate as the number of deoxycholic acid moiety was increased. Especially when tetramer of deoxycholic acid was combined with heparin, the anti-coagulant activity was even greater.

Overall, these results demonstrate that site-specific heparin conjugate with bile acid oligomer, especially ones with more than trimer of bile acids; and ones formulized for oral administration with solubilizer have a higher absoprtion rate and anti-coagulant activity compared to non-site specific heparin conjugate with bile acid oligomer.

Experimental Example 3

In Vivo Study on Oral Administration of End Site-Specific Heparin-tetraDOCA Conjugate (LHe-tetraDOCA) Formulized in a Liquid Form in Capsule to Cynomolgus Monkeys In order to determine the therapeutic effect of end site-specific heparin-oligoDOCA conjugates, heparin conjugates with deoxycholic acid tetramer was chosen to be administered. Said conjugate formulized in a liquid form in a capsule was orally administered at a dosage of 5 mg/kg to cynomolgus monkeys. The anti-FXa activity of the administered LHe-tetraDOCA conjugate was measured. As a control, a capsule containing LMWH was administered at a dosage of 10 mg.kg (n=4 rats per group). The results are shown in FIG. 14.

The end site-specific heparin-tetraDOCA conjugates showed a significantly higher anti-coagulant activity, compared to the control sample. This result indicates that the oral formulation containing the conjugate of the present invention can be effectively used for oral administration of macromolecules such as heparin.

Experimental Example 4

Confirmation of the Transport of Heparin-oligoDOCA Conjugate (LH-oligoDOCA) in Caco-2 Cell Line Experimental Example 4-1

Confirmation of the Transport of Heparin-oligoDOCA Conjugate in Caco-2 Cell

In order to determine the intestinal absorption rate of heparin-oligoDOCA onjugate, the Caco-2 cells were used. For this experiment, Caco-2 cells were plated in 12-well transwell plate (Corning, life sciences, NY) and cultured in a medium (DMEM high glucose supplemented with 10% FBS, antibiotics, NEAA) at 37° C. for 4 weeks until the cell population reaches a standard TEER value of 411±10 $\Omega cm^2$.

The 50 µg/ml of medicine was added to both TCA (Na taurocholate)-treated and untreated groups of Caco-2 cells, and then samples were incubated at 37° C. for 1 hour. Then the amount of medicine transported from apical (A) to basolateral (B) area or in a reverse direction (B to A) were measured through anti-FXa chromagenic assay.

Results of the assay demonstrate that end site-specific heparin-oligoDOCA conjugates were transported at a higher rate from A to B as the number of deoxycholic acid moeity in conjguate was increased. Especially, heparin conjugate with deoxycholic acid tetramer showed a significantly lower transport rate in a reverse direction (B to A), compared to other forms of conjugate. It indicates that heparin conjugate with deoxycholic acid tetramer has a high transport efficiency compared to the others.

Furthermore, cells were treated with 200 µM TCA which is an inhibitor of the Apical Sodium-dependent Bile Salt Transporter (ASBT). Then 50 µg/ml LMWH and LMWH-oligoDOCA conjugates were added to the cells. The inhibition of the conjugate transport from A to B was monitored and the results are shown in FIG. 17.

As shown in FIG. 17, when cells were treated with the ASBT inhibitor TCA, the transport of heparin-oligoDOCA conjugates from apical to basolateral was inhibited. Especially the inhibition of the transport was more apparent in the transport of heparin conjugate with tetramer of deoxycholic acid, indicating that the role of ASBT is significant in the transport of conjugate, especially one with tetramer of deoxycholic acid.

For identifying the transport mechanism, RITC-labeled LHe-tetraDOCA (0.05 and 0.5 mg/ml) was added to the cultured cells, which were then incubated for 30 minutes. After incubation, cells were washed three times with PBS, and stained with phalloidin-RITC (Sigma, MO) that specifically detects a tight junction in the cell. The stained cells were further treated with Vectashield (Vector Laboratories, CA) containing DAPI, and visualized under confocal laser microscopy (CLSM; Leica DM IRB/E, Leica Co, Germany). The confocal image of the cells are shown in FIG. 20.

As shown in FIG. 20, LHe-tetraDOCA were localized in cytoplasm of the cell.

Experimental Example 4-2

Confirmaiton of Absorption of End Site-Specific Heparin-OligoDOCA Conjugate in ASBT-Overexpressed MDCK Cells The relative absorption rate of the end site-specific heparin-oligoDOCA conjugate was monitored among the conjugates with different number of DOCA moiety in ASBT-overexpressed MDCK cells. These cells were cultured with a medium (DMEM high glucose supplemented with 10% FBS, antibiotics, NEAA) in 12-well transwell plate (corning, life sciences, NY) for 1 week until the TEER value reaches 411±10 $\Omega cm^2$ at 37° C. After the conjugate treatment, the amount of transported conjugate was measured as a function of time at 37° C. by anti-FXa chromagenic assay. Based on this measurement, the absorption rate of the conjugate was determined.

According to the results, in the ASBT-overexpressed MDCK cells, the end site-specific heparin-oligoDOCA conjugates showed a significantly increased absorption rate compared to the conjugate with deoxycholic acid monomer. And the absorption rate was even greater for the heparin conjugates with deoxycholic acid tetramer (FIG. 18).

The above results indicate that the end site-specific heparin-oligoDOCA conjugates in the present invention has a high absorption efficiency.

Experimental Example 5

Interaction Between End Site-Specific Heparin-OligoDOCA Conjugate and ASBT, and Uptake Through ASBT To monitor the interaction between human ASBT and LHe-tetraDOCA, LHe-tetraDOCA, which is a representative conjugate of the present invention, was added to the ASBT-overexpressed MDCK cells and incubated for 5 minutes. After cell treatment, the expression level of ASBT (slc10a2) in different cell fractions was determined by immunoblotting.

Then the uptake of the end site-specific heparin-tetra-DOCA conjugate (LHe-tetraDOCA) of the present invention was determined by the following method.

First, RITC-labeled LHe-tetraDOCA was dissolved in Hanks balanced salt solution (HBSS, Sigma, cell culture tested) supplemented with 137 mM NaCl (Sigma, cell culture tested), then the dissolved LHe-tetraDOCA was added to the cells, which were incubated for 30 minutes. Then the cells were treated with Vectashield which contains DAPI and visualized under confocal scanning laser microscopy (CSLM) to confirm the uptake of the conjugates. Meanwhile, non-transfected MDCK cells were included as a negative control. The results are shown in FIG. 19.

As shown in FIG. 19, the conjugates were localized at ASBT which is bile acid transporter. Through visualizing the interaction between the conjugate of the present invention and the transporter, it was demonstrated that an increase in absorption rate of the conjugate was not simply due to an increase in hydrophobicity, but rather due to the increased affinity of the heparin conjugate towards the bile acid transporter.

In addition to the above results, distriution of the ASBT transporters in the cell was determined. For this, LHe-tetraDOCA conjugates were added to ASBT-overexpressed MDCK cells. Then the treated cells were fractionated into cell membrane, cytoplasm, and nucleus fractions. Each cell fraction was analyzed by western blotting. Cadherin, calnexin and YY1 were used for detecting cell membrane, cytoplasm, and nucleus, respectively. Results are shown in FIG. 21.

The above result demonstrates that when LHe-tetraDOCA was removed after treatment, ASBT proteins moved from cytoplasm back to cell membrane (FIG. 21).

In addition, the expression of ASBT was monitored under fluorescence microscopy in the MDCK-ASBT cells treated with LHe-tetraDOCA conjugate of the present invention. When the cells were treated with LHe-tetraDOCA, clusters of ASBT proteins (green) were absent in the cell membrane of apical region. But once the conjugate was removed, ABST proteins were observed in the cell membrane region. Results are shown in FIG. 22. These results were not observed in a group treated with TCA or a group that was not treated with the conjugate (FIG. 22).

Interaction between LHe-tetraDOCA and ASBT was confirmed by Co-Immunoprecipitation (Co-IP) method. For this analysis, LHe-tetraDOCA was labeled with biotin and immunoprecipitates were collected by using streptavidin beads. Before running the samples on SDS-PAGE, beads mixture was heated at 70° C. for 3 minutes to dissociate biotin from streptavidin beads.

After running the samples on SDS-PAGE, membranes were probed against ASBT by using goat anti-human ASBT antibody. And mouse anti-biotin antibody (Abcam) was used for detecting co-immunoprecipitate of LHe-tetraDOCA-biotin. Purity of each cell fraction (membrane, cytoplasm, nucleus) was confirmed by specific markers. Cadherin, calnexin, and YY1 were used to detect cell membrane, cytoplasm, and nucleus fraction respectively. Results are shown in FIG. 23.

As shown in FIG. 23, interaction between ASBT and LHe-tetraDOCA conjugate of the present invention was observed in both cell membrane and cytoplasm. This result indicates that interaction between ASBT and LHe-tetra-DOCA plays a role in the transport of LHe-tetraDOCA.

For proximity ligation assay (PLA), MDCK-ASBT cells were cultured and fixed on the slide using 4% PFA in the ice bath for 20 minutes. Then the fixed cells were further treated for in situ PLA using Duolink Detection kit (Olink Bioscience, Uppsala, Sweden) referring to the manufacturer's protocol. To be more specific, after fixing the cells on the slide, cells were probed against ASBT (check name of antibody) and biotin. Then those cells were incubated with PLA probe which is formed by combining a specific oligonucleotide and a secondary antibody (anti-rabbit for ASBT and anti-mouse for biotin). Ligation of the above oligonucleotide was done by gene amplification. The results were visualized by treating the samples with fluorescent probe that is comlementary to the oligonucleotide of PLA probe. Slides were mounted using Vectashield and the samples were visualized under a confocal microscope. Results are shown in FIG. 24.

As shown in FIG. 24, the interaction between ASBT and LHe-tetraDOCA was detected as red dots. And this interaction was observed in both cell membrane and cytoplasm.

Experimental Example 6

Detection of Multi Vesicular Body (MVB) Formation of ASBT Using Transmission Electron Microscope (TEM)

LHe-tetraDOCA conjugate was added to ASBT overexpressed-MDCK cells (MDCK-ASBT cells), which were then incubated for 5 minutes at 37° C. Cells were fixed on slide by 4% PFA and incubated with rabbit anti-human ASBT antibody, which binds to N-terminal of ASBT. THen, the cells were incubated with 20 nm colloidal gold-conjugated anti-rabbit secondary antibody. Gold-labeled ASBT was monitored by using transmission electron microscope (TEM). Results are shown in FIG. 25.

As shown in FIG. 25, in the MDCK-ASBT cells that were treated with LHe-tetraDOCA which is a representative conjugate of the present invention, ASBT proteins which are normally located in the cell membrane were found in the engulfed region of the membrane and formed MVB.

These results indicate that LHe-tetraDOCA conjugates of the present invention are transported by binding to a membrane transporter ASBT and forming vesicles. This is different from a previously known transport mechanism of heparin-DOCA conjugates that were believed to be transported by diffusion.

Experimental Example 7

Exocytosis of LHe-oligoDOCA Conjugates in Baso-Lateral Part of Intestinal Cells Through Binding with IBABP In order to determine the transport mechanism of the present conjugate to blood circulation after vesicular transport, the interaction between LHe-tetraDOCA and IBABP was examined by using PLA.

To be more specific, biotin-labeled LHe-tetraDOCA was added to SK-BR3 cells that endogenously express ASBT and IBABP, and the cells were incubated for 30 minutes. Then the cells were treated with IBABP- and biotin-specific antibodies. Thereafter, the secondary PLA probes (anti-rabbit and anti-mouse) were added to detec IBABP and biotin, respectively. Then fluorescent probe was further added to amplify the signal. PLA and ASBT were stained by the method described in Experimental Example 6.

FIG. 26 shows that LHe-oligoDOCA conjugate of the present invention interacts with IBABP in SK-BR3 cells. In FIG. 26, interaction between IBABP and LHe-tetraDOCA was marked as red, and these marks were found near green marks which indicate ASBT. At a higher magnification, vesicular structure was observed.

These results indicate that LHe-tetraDOCA that was transported to the interior of the cell via ASBT interacts with IBABP to be transported to blood circulation.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non obvious combinations of elements described herein, and claims may be presented in this or a later application to any novel and non-obvious combination of these elements.

The invention claimed is:

1. An end site-specific macromolecule-bile acid oligomer conjugate, wherein:
the macromolecule is a heparin; and
the bile acid oligomer is of Formula 2:

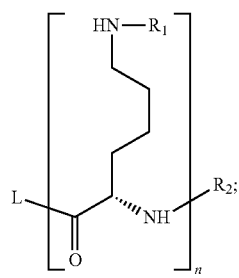

wherein:
n=2 to 3;
each of $R_1$ and $R_2$ is a bile acid residue, and $R_1$ and $R_2$ are the same bile acid residue;
L is a linker having a functional group comprising an amine group;
the linker is conjugated to the terminal site of the heparin via a carbonyl group at the end site of the heparin; and
the linker is ethylenediamine (EDA).

2. The conjugate of claim 1 that binds to apical sodium bile acid transporter (ASBT) in the intestinal cells.

3. A composition for oral administration, comprising:
an end site-specific macromolecule-bile acid oligomer conjugate in which the macromolecule is a heparin; and
a solubilizer, wherein:
the bile acid oligomer is of Formula 2:

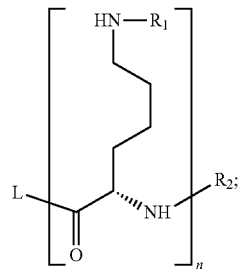

wherein:
n=2 to 3;
each of $R_1$ and $R_2$ is a bile acid residue, and $R_1$ and $R_2$ are the same bile acid residue;
L is a linker having a functional group comprising an amine group;
the linker is conjugated to the terminal site of the heparin; and
the linker is ethylenediamine (EDA).

4. The composition of claim 3, wherein the solubilizer is selected from the group consisting of polyethylene oxide, hydroxyalkyl cellulose, hydroxypropylalkyl cellulose, polyvinyl alcohol, polyvinylpyrrolidone, copovidone, sodium carboxymethyl cellulose, carbopol, sodium alginate, xanthan gum, locust bean gum, glycofurol, poloxamer, cyclodextrin and detergent.

5. A formulation for oral administration, comprising:
an end site-specific macromolecule-bile acid oligomer conjugate, wherein the macromolecule is a heparin;
a solubilizer;
an excipient;
a disintegrant;
a binder; and
a lubricant,
wherein:
the bile acid oligomer is of Formula 2:

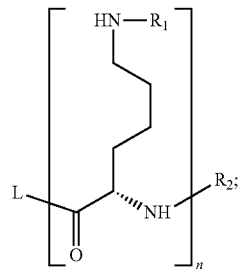

wherein:
n=2 to 3;
each of $R_1$ and $R_2$ is a bile acid residue, and $R_1$ and $R_2$ are the same bile acid residue;
L is a linker having a functional group comprising an amine group;
the linker is conjugated to the terminal site of the heparin via a carbonyl group at the end site of the heparin; and
the linker is ethylenediamine (EDA).

6. A pharmaceutical composition, comprising a heparin-bile acid oligomer conjugate, wherein:
the bile acid oligomer is of Formula 2:

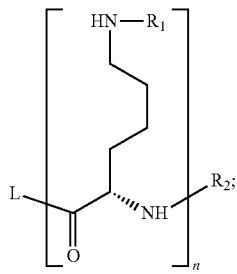

wherein:
n=2 to 3;
each of $R_1$ and $R_2$ is a bile acid residue, and $R_1$ and $R_2$ are the same bile acid residue;
L is a linker having a functional group comprising an amine group;
the linker is conjugated to the terminal site of the heparin via a carbonyl group of a reducing unit at the end site of the heparin; and
the linker is ethylenediamine (EDA).

7. A method for treating thrombosis, comprising administering the pharmaceutical composition of claim 6 to a subject suspected of thrombosis.

8. The method of claim 7, whereby after administration the heparin-bile acid oligomer conjugate is transported to the cytoplasm of intestinal cells by binding to ASBT of the intestinal cell membrane and forming vesicles.

9. The conjugate of claim 1, wherein the bile acid residue is selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid residues.

10. The conjugate of claim 1, wherein the bile acid residue is deoxycholic acid.

* * * * *